United States Patent
Cook et al.

(10) Patent No.: US 6,307,040 B1
(45) Date of Patent: *Oct. 23, 2001

(54) SUGAR MODIFIED OLIGONUCLEOTIDES THAT DETECT AND MODULATE GENE EXPRESSION

(75) Inventors: Philip Dan Cook, Vista; Andrew M. Kawasaki, Oceanside, both of CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/936,166

(22) Filed: Sep. 23, 1997

Related U.S. Application Data

(62) Division of application No. 07/835,932, filed on Mar. 5, 1992, now Pat. No. 5,670,633, which is a continuation-in-part of application No. 07/566,977, filed as application No. PCT/US91/05720 on Aug. 12, 1991, now abandoned, and a continuation of application No. 08/936,166, which is a continuation of application No. 08/468,037, filed on Jun. 6, 1995.

(51) Int. Cl.[7] .................................................. C07H 21/04
(52) U.S. Cl. ...................... 536/24.5; 536/23.1; 536/25.3
(58) Field of Search ............................... 536/23.1, 24.5, 536/25.3; 435/6, 91.1

(56) References Cited

U.S. PATENT DOCUMENTS

| | | |
|---|---|---|
| 4,381,344 | 4/1983 | Rideout et al. . |
| 5,013,830 | 5/1991 | Ohtsuka et al. . |
| 5,134,066 | 7/1992 | Rogers et al. . |
| 5,212,295 | 5/1993 | Cook . |
| 5,214,135 | 5/1993 | Srivastava et al. . |
| 5,245,022 * | 9/1993 | Weis et al. ........................... 536/24.5 |
| 5,466,786 * | 11/1995 | Buhr et al. ........................ 536/26.26 |
| 5,627,053 | 5/1997 | Usman et al. ..................... 435/91.1 |
| 5,639,647 | 6/1997 | Usman et al. ........................ 435/199 |
| 5,658,731 | 8/1997 | Sproat et al. . |
| 5,670,633 * | 9/1997 | Cook et al. .......................... 536/23.1 |
| 5,672,695 | 9/1997 | Eckstein et al. . |
| 5,698,687 | 12/1997 | Eckstein et al. . |
| 5,817,635 | 10/1998 | Eckstein et al. ....................... 514/44 |
| 5,859,221 * | 1/1999 | Cook et al. .......................... 536/23.1 |

FOREIGN PATENT DOCUMENTS

| | | |
|---|---|---|
| 2017369 | 5/1990 | (CA) . |
| 39 15462 A1 | 6/1990 | (DE) . |
| 41 10085 A1 | 10/1992 | (DE) . |
| 0 260 032 | 8/1987 | (EP) . |
| 0 287 313 | 10/1988 | (EP) . |
| 339 842 * | 11/1989 | (EP) . |
| 0 399 330 | 5/1990 | (EP) . |
| 0 417 999 | 3/1991 | (EP) . |
| 0 552 178 B1 | 1/1997 | (EP) . |
| WO 90/15814 | 12/1990 | (WO) . |
| WO 91/06556 | 5/1991 | (WO) . |
| WO 91/15499 | 10/1991 | (WO) . |
| WO 92/07065 | 4/1992 | (WO) . |

OTHER PUBLICATIONS

Arnott et al., "Optimised Parameters for A–DNA and B–DNA" *Biochemical and Biophysical Research Communication, Biochem. Biophys. Res. Commun.*, 1970, 47, 1504–1510.

Beaucage, S. et al., "Deoxynucleoside Phosphoramidites—A New Class of Key Intermediates for Deoxypolynucleotide Synthesis", *Tetra. Lett.*, 1981, 22, 1859–1862.

Butke et al., *Nucl. Acid Chem., Part 3*, 149–152.

Calvo–Mateo et al., *Tetra. Lett.*, 1988, 29, 941–944.

Chem, Q.–Y et al., *J. Chem. Soc. Perkin Trans.*, 1989, 2385–2387.

Chladek, S. et al., "Facile Synthesis of 2'–Amino–2'–Deoxyadenosine", *J. Carbo., Nucleosides & Nucleotides*, 1980, 7, 63–75.

Codington et al., *J. Org. Chem.*, 1964, 29, 558–564.

Cohen in *Oligonucleotides: Antisense Inhibitors of Gene Expression*, CRC Press, Inc., Boca Raton, FL, 1989, Table of contents only.

Dahma et al., *Can. J. Chem.*, 1989, 67, 831–839.

Divakar et al., "Reaction Between 2,2'–Anhydro–1–β–D–arabinofuranosyluracil and Thiolate Ions", *J. Chem. Soc. Perkins Trans. I*, 1982, 1625–1628.

Divakar et al., "Approaches to the Synthesis of 2'–Thio Analogues of Pyrimidine Ribosides", *J. Chem. Soc. Perkins Trans. I*, 1990, 969–974.

Freskos, J.N., "Synthesis of 2'Deoxypyrimidine Nucleosides Via Copper (I) Iodide Catalysis", *Nucleosides & Nucleotides*, 1989, 8, 1075–1076.

Gait, M.J. et al., *Oligonucleotide Synthesis A Practical Approach*, IRL Press, Washington, DC, 1984, Table of Contents only.

Guschlbauer, W. et al., "Nucleoside conformation is Determined by the Electronegativity of the Sugar Substituent", *Nucl. Acis Res.*, 1980, 8, 1421.

Hansske, F. et al., *Tetrahedron*, 1984, 40, 125.

Hertel, L.W. et al., "Synthesis of 2–Deoxy–2, 2–difluoro–D–ribose and 2–Deoxy–2,2–difluoro–D–ribofuranosyl Nucleosides", *J. Org. Chem.*, 1988, 53, 2406–2409.

Hobbs, J. et al., "Polynucleotides Containing 2'–Chloro–2'–Deoxyribose", *Biochem.*, 1972, 11, 4336.

(List continued on next page.)

Primary Examiner—David Guzo
Assistant Examiner—Andrew Wang
(74) Attorney, Agent, or Firm—Woodcock Washburn Kurtz Mackiewicz & Norris LLP

(57) ABSTRACT

Compositions and methods are provided for the treatment and diagnosis of diseases amenable to modulation of the production of selected proteins. In accordance with preferred embodiments, oligonucleotides and oligonucleotide analogs are provided which are specifically hybridizable with a selected sequence of RNA or DNA wherein at least one of the 2'-deoxyfuranosyl moieties of the nucleoside unit is modified. Treatment of HIV, herpes virus, papillomavirus and other infections is provided.

8 Claims, No Drawings

OTHER PUBLICATIONS

Ikehara, M., "Purine 8–Cyclonucleosides", *Accounts Chem. Res.*, 1969, 2, 47–53.

Ikehara et al., "Purine Cyclonucleosides–26 A Versatile Method for the Synthesis of Purine O–Cyclo–Nucleosides. The First Synthesis of 8,2'–Anhydro–8–Oxy 9–β–D–Arabinofuranosylguanine", *Tetrahedron*, 1975, 31, 1369–1372.

Ikehara et al., "Polynucleotides. L. synthesis and properties of poly (2'chloro–2'–deoxyadenylic acid) and poly (2'–bromo–2'–deoxyadenylic acid)", *Nucl. Acids Res.*, 1977, 4, 4249–4260.

Ikehara et al., "Studies of Nucleosides and Nucleotides–LXXXII.[1)] cyclonucleosides. (39) .[2)] synthesis and properties of 2'halogen–2'–deoxyadenosines", *Chem. Pharm. Bull.*, 1978, 26, 2449–2453.

Ikehara, M. et al., "Studies of Nucleosides and Nucleotides–LXXIV[1")], *Tetrahedron*, 1978, 34, 1133–1138.

Ikehara et al., "Polynucleotides. LII.synthesis and properties of poly (2'–deox–2'–fluoroadenylic acid)", *Nucl. Acids Res.*, 1978, 5, 1877–1887.

Ikehara et al., "Polynucleotides. LVI. Synthesis and Properties of Poly(2'–deoxy–2'–fluoroionosinic Acid", *Nucl. Acids Res.*, 1978, 5, 3315–3324.

Ikehara et al., "Studies on Nucleosides and Nucleotides. LXXXIX. Purine Cyclonucleosides. (43) Synthesis and Properties of 2'–Halogeno–2'–deoxyguanosines", *Chem. Pharm. Bull.*, 1981, 29(11), 3281–3285.

Imazawa et al., "Nucleosides and Nucleotides, XII. Synthesis and Properties of 2'–Deoxy–2'–mercaptouridine and its Derivatives", *Chem. Pharm. Bull.*, 1975, 23, 604–610.

Inoue, H. et al., "Synthesis and hybridization studies on two complementary nona(2'–O–methyl) ribonucleotides", *Nucl. Acids Res.*, 1987, 15, 6131–6148.

Iyer, R., Beaucage, Serge L. et al., "3H–1,2–benzodithiole–3–one 1,1–dioxide as an improved sulfurizing reagent in the solid–phase synthesis of oligodeoxyribonucleoside phosphorothioates",*J. Am. Chem. Soc.*, 1990, 112, 1253–1255.

Jarvi, E.T. et al., "Synthesis and biological evaluation of dideoxynucleosides containing a difluoromethylene unit", *Nucleosides & Nucleotides*, 1989, 8, 1111–1114.

Jones, R.A., "Transient protection: Efficient one–flask synthesis of protected deoxynucleosides", *J. Am. Chem. Soc.*, 1982, 104, 1316–1319.

Kazimierczuk et al., "Synthesis of 2'–deoxytubercidin, 2'–deoxyadenosine, and related 2'–deoxynucleosides via novel direct stereospecific sodium salt glycosylation procedure", *J. Am. Chem. Soc.*, 1984, 106, 6379–6382.

Koole et al., "Synthesis of phosphate–methylated DNA fragments using 9–fluorenylmethoxycarbonyl as transient base protecting group", *J. Org. Chem.*, 1989, 54, 1657–1664.

Markiewicz, W. and Wiewiorowski, "Nucleic Acid Chemistry", Part 3, pp. 229–231, Townsend, L. and Tipson, eds., J. Wiley and Sons, New York, 1986.

Markus–Sekura et al., "Comparative Inhibition of Chloramphenicol Acetyltransferase Gene Expression by Antisense Oligonucleotide Analogues Having Alkyl Phosphotriester, Methylphosphonate and Phosphorothioate Linkages", *Nucl. Acids Res.*, 1987, 15(4), 5749–5763.

Miller, P.S. et al., "A New Approach to Chemotherapy Based on Molecular Biology and Nucleic Acid Chemistry: Matagen (Masking Tape for Gene Expression", *Anti–Cancer Drug Design*, 1987, 2, 117–128.

Ohtsuka, M. et al., "Recognition by Restriction Endonuclease EcoRI of Deoxyoctanucleotides Containing Modified Sugar Moieties", *Eur. J. Biochem.*, 1984, 139, 447–450.

Parkes, K.E.B. et al., "A Short Synthesis of 3'–Cyano–3'–Deoxythymidine", *Tetra. Lett.*, 1988, 29, 2995–2996.

Raganthan, R., "Modification of the $2^1$–Position of Purine Nucleosides: Synthesis of $2^1$–a–Substituted–$2^1$–Deoxyadenosine Analogs", *Tetra. Lett.*, 1977, 15, 1291–1294.

Rao, T.S. et al., *J. Chem. Soc.*, 1989, 997.

Robins, M.J. et al., *Can. J. Chem.*, 1983, 61, 1911.

Ryan et al., "Synthesis of 2–Thio–D–ribose and 2'–Thioadenosine Derivatives", *J. Org. Chem.*, 1971, 36(18), 2646–2657.

Shibahara, S. et al., *Nucl. Acids Res.*, 1987, 2, 117–128.

Shibahara, S. et al., "Inhibition of Human Immunodeficiency Virus (HIV–1) Replication by Synthetic Oligo–RNA Derivatives", *Nucl. Acids Res.*, 1987, 17, 239–252.

Shibahara et al., "Inhibition of human immunodeficiency virus (IIIV–1) replication of synthetic oligo–RNA derivatives", *Nucl. Acids Res.*, 1989, 17(1), 239–252.

Sproat, B.S. et al., "Highly Efficient Chemical Synthesis of 2'–O–methyloligoribonucleotides and Tetrabiotinylated Derivatives; Novel Probes that are Resistant to Degradation by RNA or DNA Specific Nucleases", *Nucl. Acids Res.*, 1989, 17, 3373–3386.

Sproat, B.S. et al., "New synthetic routes to protected purine 2'–O–methylriboside–3'–O–phosphoramidites using a novel alkylation procedure", *Nucl. Acids Res.*, 1990, 18, 41–49.

Uesugi et al., *Tetra. Lett.*, 1979, 42, 4073.

Uesugi et al., "Improved Synthesis of 2'–Fluoro–2'–Deoxyadenosine and Synthesis and Carbon–13 NMR Spectrum of Its 3',5'–Cyclic Phosphate Derivative", *Nucleosides & Nucleotides*, 1983, 2, 373–385.

Uhlmann et al., "Antisense Oligonucleotides: A New Therapeutic Principle", *Chem. Rev.*, 1990, 558.

* cited by examiner

SUGAR MODIFIED OLIGONUCLEOTIDES THAT DETECT AND MODULATE GENE EXPRESSION

This patent application is a division of patent application Ser. No. 07/835,932, filed on Mar. 5, 1992, now U.S. Pat. No. 5,670,633, which is a continuation-in-part of application Ser. No. 07/566,977, filed on Aug. 13, 1990, now abandoned, from International patent application PCT/US91/05720, filed Aug. 12, 1991. This patent application is also a continuation of patent application Ser. No. 08/468,037, filed on Jun. 6, 1995.

FIELD OF THE INVENTION

This invention relates to the design, synthesis and application of nuclease resistant oligonucleotides which are useful for antisense oligonucleotide therapeutics, diagnostics, and research reagents. Sugar modified oligonucleotide which are resistant to nuclease degradation and are capable of modulating the activity of DNA and RNA are provided. Methods for modulating the production of proteins utilizing the modified oligonucleotide of the invention are also provided.

BACKGROUND OF THE INVENTION

It is well known that most of the bodily states in mammals including infectious disease states, are affected by proteins. Such proteins, either acting directly or through their enzymatic functions, contribute in major proportion to many diseases in animals and man.

Classical therapeutics has generally focused upon interactions with such proteins in efforts to moderate their disease causing or disease potentiating functions. Recently however, attempts have been made to moderate the actual production of such proteins by interactions with molecules that direct their synthesis, intracellular RNA. By interfering with the production of proteins, it has been hoped to effect therapeutic results with maximum effect and minimal side effects. One approach for inhibiting specific gene expression is the use of oligonucleotide and oligonucleotide analogs as antisense agents.

Antisense methodology is the complementary hybridization of relatively short oligonucleotides to single-stranded mRNA or single-stranded DNA such that the normal, essential functions of these intracellular nucleic acids are disrupted. Hybridization is the sequence specific hydrogen bonding of oligonucleotides to Watson-Crick base pairs of RNA or single-stranded DNA. Such base pairs are said to be complementary to one another.

The naturally occurring event that provides the disruption of the nucleic acid function, discussed by Cohen in *Oligonucleotides: Antisense Inhibitors of Gene Expression,* CRC Press, Inc., Boca Raton, Fla. (1989) is thought to be of two types. The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides; P. S. Miller & P. O. P. Ts'O, *Anti-Cancer Drug Design,* 2:117–128 (1987), and α-anomer oligonucleotides are the two most extensively studied antisense agents which are thought to disrupt nucleic acid function by hybridization arrest.

The second type of terminating event for antisense oligonucleotides involves the enzymatic cleavage of the targeted RNA by intracellular RNase H. The oligonucleotide or oligonucleotide analog, which must be of the deoxyribo type, hybridizes with the targeted RNA and this duplex activates the RNase H enzyme to cleave the RNA strand, thus destroying the normal function of the RNA. Phosphorothioate oligonucleotides are the most prominent example of an antisense agent which operates by this type of antisense terminating event.

Considerable research is being directed to the application of oligonucleotide and oligonucleotide analogs as antisense agents for therapeutic purposes. All applications of oligonucleotides as diagnostic, research reagents, and potential therapeutic agents require that the oligonucleotides or oligonucleotide analogs be synthesized in large quantities, be transported across cell membranes or taken up by cells, appropriately hybridize to targeted RNA or DNA, and subsequently terminate or disrupt nucleic acid function. These critical functions depend on the initial stability of oligonucleotides toward nuclease degradation.

A serious deficiency of oligonucleotides for these purposes, particularly antisense therapeutics, is the enzymatic degradation of the administered oligonucleotide by a variety of ubiquitous nucleolytic enzymes, intracellularly and extracellularly located, hereinafter referred to as "nucleases". It is unlikely that unmodified, "wild type", oligonucleotides will be useful therapeutic agents because they are rapidly degraded by nucleases. Modification of oligonucleotides to render them resistant to nucleases is therefore currently a primary focus of antisense research.

Modifications of oligonucleotides to enhance nuclease resistance have heretofore exclusively taken place on the sugar-phosphate backbone, particularly on the phosphorus atom. Phosphorothioates, methyl phosphonates, phosphorimidates, and phosphorotriesters (phosphate methylated DNA) have been reported to have various levels of resistance to nucleases. However, while the ability of an antisense oligonucleotide to bind to specific DNA or RNA with fidelity is fundamental to antisense methodology, modified phosphorous oligonucleotides, while providing various degrees of nuclease resistance, suffer from inferior hybridization properties.

Due to the prochiral nature of the phosphorous atom, modifications on the internal phosphorus atoms of modified phosphorous oligonucleotides result in Rp and Sp stereoisomers. Since a practical synthesis of stereo regular oligonucleotides (all Rp or Sp phosphate linkages) is unknown, oligonucleotides with modified phosphorus atoms have $n^2$ isomers with n equal to the length or the number of the bases in the oligonucleotide. Furthermore, modifications on the phosphorus atom have unnatural bulk about the phosphorodiester linkage which interferes with the conformation of the sugar-phosphate backbone and consequently, the stability of the duplex. The effects of phosphorus atom modifications cause inferior hybridization to the targeted nucleic acids relative to the unmodified oligonucleotide hybridizing to the same target.

The relative ability of an oligonucleotide to bind to complementary nucleic acids is compared by determining the melting temperature of a particular hybridization complex. The melting temperature ($T_m$), a characteristic physical property of double helixes, denotes the temperature in degrees centigrade at which 50% helical versus coil (unhybridized) forms are present. $T_m$ is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$. The higher the $T_m$, the greater the strength of the binding of the strands. Non-Watson-Crick base pairing has a strong destabilizing effect on the $T_m$. Consequently, absolute fidelity of base pairing is necessary to have optimal binding of an antisense oligonucleotide to its targeted RNA.

Considerable reduction in the hybridization properties of methyl phosphonates and phosphorothioates has been reported by Cohen. Methyl phosphonates have a further disadvantage in that the duplex formed with RNA does not activate degradation by RNase H as an terminating event, but instead acts by hybridization arrest which can be reversed due to a helical melting activity located on the ribosome. Phosphorothioates are highly resistant to most nucleases. However, phosphorothioates typically exhibit on-antisense modes of action, particularly the inhibition of various enzyme functions due to nonspecific binding. Enzyme inhibition by sequence-specific oligonucleotides undermines the very basis of antisense chemotherapy.

Therefore, oligonucleotides modified to exhibit resistance to nucleases, to activate the RNase H terminating event, and to hybridize with appropriate strength and fidelity to its targeted RNA (or DNA) are greatly desired for antisense oligonucleotide therapeutics.

M. Ikehara et al., *European Journal of Biochemistry* 139:447–450(1984) report the synthesis of a mixed octamer containing one 2'-deoxy-2'-fluoroguanosine residue or one 2'-deoxy-2'-fluoroadenine residue. W. Guschlbauer and K. Jankowski, *Nucleic Acids Res.* 8:1421 (1980) have shown that the contribution of the N form (3'-endo, 2'-exo) increases with the electronegativeness of the 2'-substituent. Thus, 2'-deoxy-2'-fluorouridine contains 85% of the C3'-endo conformer. M. Ikehara et al., *Tetrahedron Letters* 42:4073 (1979) have shown that a linear relationship between the electronegativeness of 2'-substituents and the % N conformation (3'-endo-2'-exo) of a series of 2'-deoxy-adenosines. M. Ikehara et al., *Nucleic Acids Research* 5:1877 (1978) have chemically transformed 2'-deoxy-2'-fluoro- adenosine to its 5'-diphosphate. This was subsequently enzymatically polymerized to provide poly(2'-deoxy-2'- fluoroadenylic acid).

Furthermore, evidence was presented which indicates that 2'-substituted 2'-deoxyadenosines polynucleotides resemble double stranded RNA rather than DNA. M. Ikehara et al., *Nucleic Acids Res.* 5:3315 (1978) show that a 2'-fluorine substituent in poly A, poly I, and poly C duplexed to their U, C, or I complement are significantly more stable than the ribo or deoxy poly duplexes as determined by standard melting assays. M. Ikehara et al., *Nucleic Acids Res.* 4:4249 (1978) show that a 2'-chloro or bromo substituents in poly(2'-deoxyadenylic acid) provides nuclease resistance. F. Eckstein et al., *Biochemistry* 11:4336 (1972) show that poly(2'-chloro-2'-deoxyuridylic acid) and poly(2'-chloro-2'-deoxycytidylic acid) are resistant to various nucleases. H. Inoue et al., *Nucleic Acids Research* 15:6131 (1987) describe the synthesis of mixed oligonucleotide sequences containing 2'-OMe at every nucleotide unit. The mixed 2'-OMe substituted sequences hybridized to their ribooligonucleotide complement (RNA) as strongly as the ribo-ribo duplex (RNA-RNA) which is significantly stronger than the same sequence ribo-deoxyribo heteroduplex ($T_m$s, 49.0 and 50.1 versus 33.0 degrees for nonamers). S. Shibahara et al., *Nucleic Acids Research* 17:239 (1987) describe the synthesis of mixed oligonucleotides sequences containing 2'-OMe at every nucleotide unit. The mixed 2'-OMe substituted sequences were designed to inhibit HIV replication.

It is thought that the composite of the hydroxyl group's steric effect, its hydrogen bonding capabilities, and its electronegativeness versus the properties of the hydrogen atom is responsible for the gross structural difference between RNA and DNA. Thermal melting studies indicate that the order of duplex stability (hybridization) of 2'-methoxy oligonucleotides is in the order of RNA-RNA, RNA-DNA, DNA-DNA.

The 2'-deoxy-2'-halo, azido, amino, methoxy homopolymers of several natural occurring nucleosides have been prepared by polymerase processes. The required 2'-modified nucleosides monomers have not been incorporated into oligonucleotides via nucleic acids synthesizer machines. Thus, mixed sequence (sequence-specific) oligonucleotides containing 2'-modifications at each sugar are not known except for 2'-deoxy-2'-methoxy analogs.

OBJECTS OF THE INVENTION

It is a principal object of the invention to provide nuclease resistant, sugar modified oligonucleotides or oligonucleotide analogs for use in antisense oligonucleotide diagnostics, research reagents, and therapeutics.

It is a further object of the invention to provide such oligonucleotides or oligonucleotides analogs which are effective in modulating the activity of a DNA or an RNA.

Another object of the invention is to provide such oligonucleotides or oligonucleotide analogs which are less likely to invoke undesired or toxic side reactions.

Yet another object of the invention is to provide research and diagnostic methods and materials for assaying bodily states in animals, especially diseased states.

A further object of the invention is to provide therapeutic and research methods and materials for the treatment of diseases through modulation of the activity of DNA and RNA.

These and other objects will become apparent to persons of ordinary skill in the art from a review of the present specification and attendant claims.

SUMMARY OF THE INVENTION

In accordance with the present invention, compositions which are resistant to nuclease degradation and but which modulate the activity of DNA and RNA are provided. These compositions are comprised of sugar modified oligonucleotides or oligonucleotide analogs, the targeting portions of which are specifically hybridizable with preselected nucleotide sequences of single-stranded or double-stranded DNA or RNA. The sugar modified oligonucleotides recognize and form double strands with single stranded DNA and RNA or triple strands with double stranded DNA and RNA.

The nuclease resistant oligonucleotides of this invention consist of a single strand of nucleic acid bases linked together through linking groups. The target portion of the nuclease resistant oligonucleotide may range in length from about 5 to about 50 nucleic acid bases. However, in accordance with the preferred embodiment of this invention, a target sequence of about 15 bases in length is optimal.

The nucleic acid bases may be pyrimidines such as thymine, uracil or cytosine, or purines such as guanine or adenine, or both, arranged in a specific sequence. The sugar moiety of such bases may be of the deoxyribose or ribose type. The groups linking the bases together may be the usual sugar phosphate nucleic acid backbone, but may also be modified as a phosphorothioate, methylphosphonate, or phosphate alkylated moiety to further enhance the sugar modified oligonucleotide properties, along with removal of a 5'-methylene group and/or carbocyclic sugar.

In accordance with this invention, the targeting portion is an analog of an oligonucleotide wherein at least one of the 2'-deoxy ribofuranosyl moieties of the nucleoside unit is modified. A hydrogen or a hydroxyl, halo, azido, amino, methoxy or alkyl group may be added. For example, H, OH, F, CN, $CF_3$, $OCF_3$, OCN, O-alkyl, S-alkyl, SOMe, $SO_2Me$, $ONO_2$, $NO_2$, $N_3$, $NH_2$, NH-alkyl, $OCH_2CH=CH_2$ (allyloxy), $OCH=CH_2$, OCCH where alkyl is a straight or branched chain of C1 to C12 may be used, with unsaturation within the carbon chain, such as allyloxy being particularly preferred.

The resulting novel oligonucleotides or oligonucleotide analogs are resistant to nuclease degradation and exhibit hybridization properties of higher quality relative to wild type (DNA-DNA and RNA-DNA) duplexes and the phosphorus modified oligonucleotide antisense duplexes containing phosphorothioates, methylphosphonates, phophoramidates and phosphorotriesters.

The invention is also directed to methods for modulating the production of a protein by an organism comprising contacting the organism with a composition formulated in accordance with the foregoing considerations. It is preferred that the RNA or DNA portion which is to be modulated be preselected to comprise that portion of DNA or RNA which codes for the protein whose formation is to be modulated. The targeting portion of the composition to be employed is, thus, selected to be complementary to the preselected portion of DNA or RNA, that is to be an antisense oligonucleotide for that portion.

This invention is also directed to methods of treating an organism having a disease characterized by the undesired production of a protein. This method comprises contacting the organism with a composition in accordance with the foregoing considerations. The composition is preferably one which is designed to specifically bind with messenger RNA which codes for the protein whose production is to be inhibited.

The invention further is directed to diagnostic methods for detecting the presence or absence of abnormal RNA molecules or abnormal or inappropriate expression of normal RNA molecules in organisms or cells.

The invention is also directed to methods for the selective binding of RNA for research and diagnostic purposes. Such selective, strong binding is accomplished by interacting such RNA or DNA with compositions of the invention which are resistant to degradative nucleases and hybridize stronger and with greater fidelity than any other known oligonucleotide or oligonucleotide analog.

Additionally this invention is directed to a method of synthesis of 2'-deoxy-2'-substituted nucleosides, particularly guanosine compounds. In accordance with this method, the 2'-hydroxyl moiety of guanosine is first oxidized and then reduced with inversion about the 2' position to yield 9-(β-D-arabinofuranosyl)guanine. The 2' arabino hydroxyl group is derivatized with a leaving group. Nucleophilic displacement of the leaving group with a nucleophile is accomplished with a further inversion to give the 2'-deoxy-2'-substituted guanosine compound.

DETAILED DESCRIPTION OF PREFERRED EMBODIMENTS

The compositions useful for modulating the activity of an RNA or DNA molecule in accordance with this invention generally comprise a sugar modified oligonucleotide containing a target sequence which is specifically hybridizable with a preselected nucleotide sequence of single stranded or double stranded DNA or RNA molecule and which is nuclease resistant.

It is generally desirable to select a sequence of DNA or RNA for or which is involved in the production of proteins whose synthesis is ultimately to be modulated or inhibited in entirety. The targeting portion of the composition is generally an oligonucleotide analog. It is synthesized, conveniently through solid state synthesis of known methodology, to be complementary to or at least to be specifically hybridizable with the preselected nucleotide sequence of the RNA or DNA. Nucleic acid synthesizers are commercially available and their use is generally understood by persons of ordinary skill in the art as being effective in generating nearly any oligonucleotide of reasonable length which may be desired.

In the context of this invention, the term "oligonucleotide" refers to a plurality of joined nucleotide units formed in a specific sequence from naturally occurring bases and pentofuranosyl groups joined through a sugar group by native phosphodiester bonds. These nucleotide units may be nucleic acid bases such as guanine, adenine, cytosine, thymine or uracil. The sugar group may be deoxyribose or ribose. This term refers to both naturally occurring or synthetic species formed from naturally occurring subunits.

"Oligonucleotide analog" as the term is used in connection with this invention, refers to moieties which function similarly to oligonucleotides but which have non-naturally occurring portions. Oligonucleotide analogs may have altered sugar moieties or inter-sugar linkages, for example, phosphorothioates and other sulfur containing species which are known for use in the art. Oligonucleotide analogs may also comprise altered base units or other modifications consistent with the spirit of this invention, and in particular such modifications as may increase nuclease resistance of the oligonucleotide composition in order to facilitate antisense therapeutic, diagnostic or research reagent use of a particular oligonucleotide.

It is generally preferred for use in some embodiments of this invention that some positions of the nucleotide base be substituted in order to increase the nuclease resistance of the composition while maintaining the integrity of the oligonucleotide binding capabilities.

It is preferred in some embodiments of the present invention to employ further modified oligonucleotides. In this context, modified oligonucleotide analogs refers to a structure which is generally similar to native oligonucleotides, but which have been modified in one or more significant ways.

Such modifications may take place at the sugar backbone of the invention. It is generally preferred to enhance the ability of the target sequence of the sugar modified oligonucleotides to penetrate into the intracellular spaces of cells where the messenger RNA or DNA, which are the targets of the overall composition, reside. Therefore, it is generally preferred to provide modifications of oligonucleotides which are substantially less ionic than native forms in order to facilitate penetration of the oligonucleotide into the intracellular spaces. Any of the existing or yet to be discovered methods for accomplishing this goal may be employed in accordance with the practice of the present invention. At present, it has been found preferable to employ substitutions for the phosphorodiester bond, which substitutions are not only relatively less ionic than the naturally occurring bonds but are also substantially non-chiral.

As will be appreciated, the phosphorus atom in the phosphorodiester linkage is "pro-chiral". Modifications at the phosphorus, such as is done in methyl phosphonates and phosphorothioates type oligonucleotides, results in essentially chiral structures. Chirality results in the existence of two isomers at each chiral center which may interact differently with cellular molecules. Such an unresolved mixture of isomers may inhibit the transport of the resulting compositions into the intracellular spaces or decrease the affinity and specificity of hybridization to the specific target RNA or DNA. Thus, it is preferred in some embodiments of this invention to employ substantially non-ionic, substantially non-chiral entities in lieu of some or all of the phosphorodiester bonds. For this purpose, short chain alkyl or cycloalkyl structures especially $C_2$–$C_4$ structures are preferred. As is set forth in an application filed on even date herewith and assigned to a common assignee hereof, said application being entitled "Polyamine Oligonucleotides to Enhance Cellular Uptake," application Ser. No. 558,663 filed Jul. 27, 1990 the modification of the sugar structure including the elimination of one of the oxygen functionality may permit the introduction of such substantially non-chiral, non-ionic substituents in this position. The entirety of the disclosure of application Ser. No. 558,663 is incorporation herein by reference in order to disclose more fully such modifications.

In keeping with the goals of the invention are the standard backbone modifications such as substituting P for S, Me-P, MeO-P, $H_2N$-P, etc. These substitutions are thought in some cases to enhance the sugar modified oligonucleotide properties.

The targeting portion of the compositions of the present invention, are preferably oligonucleotide analogs having 5 to about 50 base units. It is more preferred that such functionalities have from 8 to about 40 base units and even more preferred that from about 12 to 20 base units be employed. Oligonucleotides or oligonucleotide analogs having about 15 base units are preferable for the practice of certain embodiments of the present invention.

It is desired that the targeting portion be adapted so as to be specifically hybridizable with the preselected nucleotide sequence of the RNA or DNA selected for modulation. Oligonucleotide analogs particularly suited for the practice of one or more embodiments of the present invention comprise 2'-sugar modified oligonucleotides wherein one or more of the 2'-deoxy ribofuranosyl moieties of the nucleoside unit is modified with a hydrogen or hydroxyl, halo, azido, amino, alkyoxy, thioalkoxy, alkylamino or alkyl group. For example, the substitutions which may occur include H, OH, F, CN, $CF_3$, $OCF_3$, OCN, O-alkyl, S-alkyl, SOMe, $SO_2Me$, $ONO_2$, $NO_2$, $N_3$, $NH_2$, NH-alkyl, OCH=$CH_2$, OCCH where alkyl is a straight or branched chain of $C_1$ to $C_{12}$ with unsaturation within the carbon chain such as allyloxy.

These modified bases are linked together and to the rest of the oligonucleotide or oligonucleotide analog through a sugar linking group. The linking group may be any of those structures described herein which are capable of linking sugar moieties of oligonucleotides together to form the targeting portion of the compositions of this invention. It is preferred that these sugar linking groups comprise the phosphodiester structure or a derivative of such. Derivatives of the phosphodiester structure may include substitution of a sulphur, an alkoxy group such as methyl, methyl oxide, or amine group for an oxygen. The sugar phosphate nucleic acid backbone may be modified as a phosphorothioate, alkylphosphonate such as methylphosphonate or phosphate alkylated moiety (a phosphotriester). The phosphodiester linkage may also be replaced by a carbon or ether linkage.

In further embodiment of this invention, a linking moiety has been devised to allow the direct attachment of a modified unit to the terminal position of the 3'-end of the modified oligonucleotides. Thus, an ester, or more preferably a bromomethylketo group, is attached to the 3'-hydroxyl of a modified 2'-modified nucleoside having its 5'-hydroxyl protected with a dimethoxytriphenylmethyl group and, if the heterocycle is of the cytosine series, having that heterocycle protected with a benzoyl protecting group. If the required targeting sequence has a terminal 3'-thymine or cytosine base, the desired modified thymine or cytosine base containing the bromomethylketo linker is utilized as the first monomer to attach to the control pore glass (CPG) solid support which contains a normal nucleoside attached via its 3'-hydroxyl group. The base sensitive ester linkage attaching the 2'-modified nucleoside to the nucleoside attached to the CPG is cleaved under the usual concentrated ammonium hydroxide conditions that are utilized to remove the oligonucleotide from the CPG support. This will allow the modified oligonucleotide to have a 2'-modified unit at its terminal, 3'-end.

Cleavage of oligonucleotides by nucleolytic enzymes require the formation of an enzyme-substrate complex, or in particular a nuclease-oligonucleotide complex. The nuclease enzymes will generally require specific binding sites located on the oligonucleotides for appropriate attachment. If the oligonucleotide binding sites are removed or hindered such that the nucleases will not attach to the oligonucleotides, the nuclease resistant oligonucleotides result. In the case of restriction endonucleases that cleave sequence-specific palindromic double-stranded DNA, certain binding sites such as the ring nitrogen in the 3- and 7-positions have been identified as required biding sites. Removal of one or more of these sites or hindering the nuclease approach to these particular positions within the recognition sequence has provided various levels or resistance to the specific nucleases.

This invention provides antisense oligonucleotides characterized by superior hybridizing properties. We have discovered from structure activity relationships studies that a significant increase in binding ($T_m$)s of certain 2'-sugar modified oligonucleotides to its RNA target (complement) is correlated with an increased "A" type conformation of the heteroduplex. Furthermore, absolute fidelity of the modified oligonucleotides is maintained. The increased binding of our 2'-sugar modified sequence-specific oligonucleotides provides superior potency and specificity compared to phosphorus modified antisense oligonucleotides such as methyl phosphonates, phosphorothioates, phosphate triesters and phosphoramidites as known in the literature.

The only structural difference between DNA and RNA duplexes is an hydrogen atom in the 2'-position of the DNA ribofuranosyl moieties versus a hydroxyl group in the 2'-position of the RNA ribofuranosyl moieties (assuming that the presence or absence of a methyl group in the uracil ring system has no effect). However, gross conformational differences exist between DNA and RNA duplexes.

It is known from X-ray diffraction analysis of nucleic acid fibers, Arnott and Hukins, *Biochemical and Biophysical Research Communication,* 47:1504–1510 (1970), and analysis of crystals of double-stranded nucleic acids that DNA takes a "B" form structure and that RNA only takes the much more rigid "A" form structure. The difference between the sugar puckering (C2' endo for "B" form DNA and C3' endo for A-form RNA) of the nucleoside monomeric units of DNA and RNA is the major conformational difference between double-stranded nucleic acids.

The primary contributor to the pentofuranosyl moiety conformation is the nature of the substituent in the 2'-position. Thus, the population of the C3'-endo form increases with respect to the C2'-endo as the electronegativity of the 2'-substituent increases. For example, among 2'-deoxy-2'-halo-adenine nucleosides, the 2'-fluoro derivative exhibits the largest population (65%) of C3'-endo, and the 2'-iodo shows the lowest (7%). Those of the adenosine (2'-OH) and deoxyadenosine (2'-H) are 36% and 19%, respectively. Furthermore, the effect of the 2'-fluoro group of adenine dinucleotides (2'-deoxy-2'-fluoroadenosine-2'-deoxy-2'- fluoroadenosine or uridine) is further correlated to the stabilization of the stacked conformations more than ribo or deoxyribo modified dimers. Research indicates that the dinucleosides phosphates have a stacked conformation with a geometry similar to that of A—A but with a greater extent of base-base overlapping than A—A. It was assumed that the highly polar nature of the C2'-F bond and the extreme preference for C3'-endo puckering may stabilize the stacked conformation in an "A" structure.

Data from UV hypochromicity, circular dichromism, and $^1$H NMR also indicate that the degree of stacking decreases as the electronegativeness of halogen decreases. Furthermore, a steric bulkiness in the 2'-position is better accommodated in an "A" form duplex than a "B" form duplex.

Thus, a 2'-substituent on the 3'-nucleotidyl unit of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent.

The 2'-iodo substituted nucleosides possess the lowest C3'-endo population (7%) of the halogen series. Thus, on steric effects alone, one would predict an 2'-iodo or similar groups would contribute stacking destabilizing properties and thus reduced binding ($T_m$s) for antisense oligonucleotides. However, the lower electronegativeness and high hydrophobic attractive forces of the iodine atom and similar groups complicates the ability to predict stacking stabilities and binding strengths.

Studies with the 2'-OMe modification of 2'-deoxy guanosine, cytidine, and uridine dinucleoside phosphates exhibit enhanced stacking effects with respect to the corresponding unmethylated species (2'-OH). In this case, the hydrophobic attractive forces of the methyl group tend to overcome the destablilizing effects of its steric bulkiness (hindrance).

2'-Fluoro-2'-deoxyadenosine has been determined to have an unusually high population of 3'-endo puckering among nucleosides. Adenosine, 2'-deoxyadenosine, and other derivatives typically have population below 40% in the 3'-endo conformer. It is known that a nucleoside residue in well-stacked oligonucleotides favors 3'-endo ribofuranose puckering.

Melting temperatures (complementary binding) are increased with the 2'-substituted adenosine diphosphates. It is not clear whether the 3'-endo preference of the conformation or the presence of the substituent is responsible for the increased binding. However, as noted, greater overlap of adjacent bases (stacking) can be achieved with the 3'-endo conformations.

The present novel approach to obtaining stronger binding is to prepare antisense RNA mimics to bind to the targeted RNA. Therefore, a random structure-activity relationship approach was undertaken to discover nuclease resistant antisense oligonucleotides that maintained appropriate hybridization properties.

A series of 2'-deoxy-2'-modified nucleosides of adenine, guanine, cytosine, thymidine and certain analogs of these bases have been prepared and have been inserted as the modified nucleosides into sequence-specific oligonucleotides via solid phase nucleic acid synthesis. The novel antisense oligonucleotides were assayed for their ability to resist degradation by nucleases and to possess hybridization properties comparable to the unmodified parent oligonucleotide. Initially, small electronegative atoms or groups were selected because these type are not likely to sterically interfere with required Watson-Crick base pair hydrogen bonding (hybridization). However, electronic changes due to the electronegativeness of the atom or group in the 2'-position may profoundly effect the sugar conformation. During our structure activity relationship studies we discovered that the sugar modified oligonucleotides hybridized to the targeted RNA stronger than the unmodified (2'-deoxyribosyl type).

2'-Substituted oligonucleotides are synthesized by the standard solid phase, automated nucleic acid synthesizer such as the Applied Biosystems, Incorporated 380B or MilliGen/ Biosearch 7500 or 8800. Triester, phosphoramidite, or hydrogen phosphonate coupling chemistries (oligonucleotides. Antisense Inhibitors of Gene Expression. M. Caruthers, pp 7–24, Edited by J. S. Cohen, CRC Press, Inc. Boca Raton, Fla., 1989) are used in with these synthesizers to provide the desired oligonucleotides. The Beaucage reagent (Journal of American Chemical Society, 112, 1253–1255, 1990) or elemental sulfur (S. Beaucage et al., Tetrahedron Letters, 22,1859–1862, 1981) is used with phosphoramidite or hydrogen phosphonate chemistries to provide 2'-substituted phosphorothioate oligonucleotides.

The requisite 2'-substituted nucleosides (A, G, C, T(U), and nucleic acid base analogs) are generally prepared by modification of several literature procedures as described below.

Procedure 1. Nucleophilic Displacement of 2'-Leaving Group in Arabino Purine Nucleosides. Nucleophilic displacement of a leaving group in the 2'-up position (2'-deoxy-2'-(leaving group)arabino sugar) of adenine or guanine or their analog nucleosides. General synthetic procedures of this type have been described by M. Ikehara et al., *Tetrahedron* 34:1133–1138 (1978); ibid., 31:1369–1372 (1975); *Chemistry and Pharmaceutical Bulletin,* 26:2449–2453 (1978); ibid., 26:240–244 (1978); M. Ikehara *Accounts of Chemical Research,* 2:47–53 (1969); and R. Ranganathan *Tetrahedron Letters,* 15:1291–1294 (1977).

Procedure 2. Nucleophilic Displacement of 2,2'-Anhydro Pyrimidines. Nucleosides thymine, uracil, cytosine or their analogs are converted to 2'-substituted nucleosides by the intermediacy of 2,2'-cycloanhydro nucleoside as described by J. J. Fox, et al., *Journal of Organic Chemistry,* 29:558–564 (1964).

Procedure 3. 2'-Coupling Reactions. Appropriately 3',5'-sugar and base protected purine and pyrimidine nucleosides having a unprotected 2'-hydroxyl group are coupled with electrophilic reagents such as methyl iodide and diazomethane to provide the mixed sequences containing a 2'-OMe group H. Inoue, et al., *Nucleic Acids Research* 15: 6131–6148.

Procedure 4. 2-Deoxy-2-substituted Ribosylations. 2-Substituted-2-deoxyribosylation of the appropriately protected nucleic acid bases and nucleic acids base analogs has been reported by E. T. Jarvi, et al., *Nucleosides & Nucleotides* 8:1111–1114 (1989) and L. W. Hertel, et al., *Journal of Organic Chemistry* 53:2406–2409 (1988).

Procedure 5. Enzymatic Synthesis of 2'-Deoxy-2'-Substituted Nucleosides. The 2-Deoxy-2-substituted glycosyl transfer from one nucleoside to another with the aid of pyrimidine and purine ribo or deoxyribo phosphorolyses has been described by J. R. Rideout and T. A. Krenitsky, U.S. Pat. No. 4,381,344 (1983).

Procedure 6. Conversion of 2'-Substituents Into New Substituents. 2'-Substituted-2'-deoxynucleosides are converted into new substituents via standard chemical manipulations. For example, S. Chladek et al., *Journal of Carbohydrates, Nucleosides & Nucleotides* 7:63–75 (1980) describes the conversion of 2'-deoxy-2'-azidoadenosine, prepared from arabinofuranosyladenine, into 2'-deoxy-2'-aminoadenosine.

Procedure 7. Free Radical Reactions. Conversions of halogen substituted nucleosides into 2'-deoxy-2'-substituted nucleosides via free radical reactions has been described by K. E. B. Parkes and K. Taylor, *Tetrahedron Letters* 29:2995–2996 (1988).

Procedure 8. Conversion of Ribonucleosides to 2'-Deoxy-2'-Substituted Nucleoside. Appropriately 3',5'-sugar and base protected purine and pyrimidine nucleosides having a unprotected 2'-hydroxyl group are converted to 2'-deoxy-2'-substituted nucleosides by the process of oxidation to the 2'-keto group, reaction with nucleophilic reagents, and finally 2'-deoxygenation. Procedures of this type have been described by F. De las Heras, et al., *Tetrahedron Letters* 29:941–944 (1988).

Procedure 9. In a preferred process of the invention, 2'-deoxy-Substituted guanosine compounds are prepared via n (arabinofuranosyl)guanine intermediate obtained via an oxidation-reduction reaction. A leaving group at the 2' position of the arabinofuranosyl sugar moiety of the intermediate arabino compound is displaced via an $SN_2$ reaction with an appropriate nucleophile. This procedure thus incorporate principles of both Procedure 1 and Procedure 8 above. 2'-Deoxy-2'-fluoroguanosine is preferably prepared via this procedure. The intermediate arabino compound was obtained utilizing a variation of the oxidation-reduction procedure of Hansske, F., Madej, D. and Robins, M. J. (1984), *Tetrahedron,* 40:125. According to this invention, the reduction was effected starting at −78° C. and allowing the reduction reaction to exothermically warm to about −2° C. This results in a high yield of the intermediate arabino compound.

In conjunction with use of a low temperature reduction, utilization of a tetraisopropyldisiloxane blocking group (a "TPDS" group) for the 3' and 5' positions of the starting guanosine compound contributes in an improved ratio of intermediate arabino compound verses the ribo compound following oxidization and reduction. Following oxidation/reduction, the $N^2$ guanine amino nitrogen and the 2'-hydroxyl moieties of the intermediate arabino compound are blocked with isobutyryl protecting groups ("Ibu" groups). The tetraisopropyldisiloxane blocking group is removed and the 3' and 5' hydroxyl's are further protected with a second blocking group, a tetrahydropyranyl blocking group (a "THP" group). The isobutyryl group is selectively removed from 2'-hydroxyl group followed by derivation of the 2' position with a triflate (a trifluoromethylsulfonyl) leaving group. The triflate moiety was then displaced with inversion about the 2' position to yield the desire 2'-deoxy-2'-fluoroguanosine compound.

In addition to the triflate leaving group, other leaving groups include but are not necessarily limited to alkysulfonyl, substituted alkylsulfonyl, arylsulfonyl, substituted arylsulfonyl, heterocyclosulfonyl or trichloroacetimidate. Representative examples include p-(2,4-dinitroanilino) benzenesulfonyl, benzenesulfonyl, methylsulfonyl, p-methylbenzenesulfonyl, p-bromobenzene-sulfonyl, trichloroacetimidate, acyloxy, 2,2,2-trifluoro-ethanesulfonyl, imidazolesulfonyl and 2,4,6-trichlorophenyl.

The isobutyryl group remaining on the $N^2$ heterocyclic amino moiety of the guanine ring can be removed to yield a completely deblocked nucleoside; however, preferably for incorporation of the 2'-deoxy-2'-substituted compound in an oligonucleotide, deblocking of the $N^2$ isobutyryl protecting group is deferred until after oligonucleotide synthesis is complete. Normally for use on automated nucleic acid synthesizers, blocking of the $N^2$ guanine amino moiety with an isobutyryl group is preferred. Thus advantageously, the $N^2$-isobutyryl blocked 2'-deoxy-2'-substituted guanosine compounds resulting from the method of the invention can be directly used for oligonucleotide synthesis on automatic nucleic acid synthesizers.

The oligonucleotides or oligonucleotide analogs of this invention can be used in diagnostics, therapeutics, and as research reagents and kits. For therapeutic use the oligonucleotide is administered to an animal suffering from a disease affected by some protein. It is preferred to administer to patients suspected of suffering from such a disease with amounts of oligonucleotide which are effective to reduce the symptemology of that disease. It is within the scope of a person's skill in the art to determine optimum dosages and treatment schedules for such treatment regimens.

It is generally preferred to apply the therapeutic agents in accordance with this invention internally such as orally, intravenously, or intramuscularly. Other forms of administration, such as transdermally, topically, or intralesionally may also be useful. Inclusion in suppositories may also be useful. Use of pharmacologically acceptable carriers is also preferred for some embodiments.

The following examples illustrate the practice of this invention.

EXAMPLE 1

Preparation of 2'-Deoxy-2'-fluoro Modified Oligonucleotides

A. $N^6$-Benzoyl-[2'-deoxy-2'-fluoro-5'-O-(4,4'-dimethoxytrityl)]adenosine-3'-O-(N,N-diisopropyl-β-cyanoethyl phosphoramidite.

$N^6$-Benzoyl-9-(2'-fluoro-β-D-ribofuranosyl)adenine was prepared from 9-β-D-arabinofuranosyladenine in a five-step synthesis using a modification of a procedure reported by M. Ikehara at al., *Nucleosides and Nucleotides* 2:373–385 (1983). Thus, the $N^6$-benzoyl derivative was obtained in good yield utilizing the method of transient protection with chlorotrimethylsilane. R. A. Jones, *J. Am. Chem. Soc.* 104:1316 (1982). Selective protection of the 3' and 5'-hydroxyl groups of $N^6$-Benzoyl-9-β-D-arabinofuranosyladenine with tetrahydropyranyl (THP) was accomplished by modification of a literature procedure G. Butke, et al., in *Nucleic Acid Chemistry, Part* 3:149–152, Townsend, L. B. and Tipson, R. S. eds., (J. Wiley and Sons, New York 1986) to yield $N^6$-Benzoyl-9-[3',5'-di-O-(tetrahydropyran-2-yl)-β-D-arabino furanosyl]adenine in good yield. Treatment of $N^6$-Benzoyl-9-[3',5'-di-O-(tetrahydropyran-2-yl)-β-D-arabinofuranosyl]adenine with trifluoromethanesulfonic anhydride in dichloromethane gave the 2'-triflate derivative $N^6$-Benzoyl-9-[2'-O-trifluoromethylsulfonyl-3',5'-di-O-tetrahydropyran-2-yl)-β-D-arabino furanosyl]adenine which was not isolated due to its lability. Displacement of the 2'-triflate group was effected by reaction with tetrabutylammonium fluoride in tetrahydrofuran to obtain a moderate yield of the 2'-fluoro derivative $N^6$-Benzoyl-9-[2'-fluoro-3',5'-di-o-tetrahydro-pyran-2-yl)-β-D-arabinofuranosyl]adenine. Deprotection of the THP groups of $N^6$-Benzoyl-9-[2'-fluoro-3',5'-di-O-(tetrahydropyran-2-yl)-β-D-arabino furanosyl]adenine was accomplished by treatment with Dowex-50W in methanol to yield $N^6$-benzoyl-9-(2'-deoxy-2'-fluoro-β-D-ribofuranosyl) adenine in moderate yield. The $^1$H-NMR spectrum of 6 was in agreement with the literature values. M. Ikehara and H. Miki, *Chem. Pharm. Bull.* 26: 2449–2453 (1978). Standard methodologies were employed to obtain the 5'-dimethoxytrityl-3'-phosphoramidite intermediates $N^6$-Benzoyl-9-[2'-fluoro-5'-O-(4,4'-dimethoxytrityl)-β-D-ribofuranosyl]adenine and $N^6$-Benzoyl-[2'-deoxy-2'-fluoro-5'-O-(4,4'-dimethoxytrityl)]adenosine-3'-O-(N,N-diisopropyl-β-cyanoethylphosphoramidite. K. K. Ogilvie, *Can J. Chem.* 67: 831–839 (1989).

B. $N^6$-Benzoyl-9-β-D-arabinofuranosyladenine.

9-β-D-arabinofuranosyladenine (1.07 g, 4.00 m.mol) was dissolved in anhydrous pyridine (20 mL) and anhydrous dimethylformamide (20 ml) under an argon atmosphere. The solution was cooled to ice temperature and chlorotrimethylsilane (3.88 ml, 30.6 m.mol) was added slowly to the reaction mixture via syringe. After stirring the reaction mixture at ice temperature for 30 minutes, benzoyl chloride (2.32 ml, 20 m.mol) was added slowly. The reaction mixture was allowed to warm to 20° C. and stirred for 2 hours. After cooling the reaction mixture to ice temperature, cold water (8 ml) was added and the mixture was stirred for 15 minutes. Concentrated ammonium hydroxide (8 ml) was slowly added to the reaction mixture to give a final concentration of 2M of ammonia. After stirring the cold reaction mixture for 30 minutes, the solvent was evaporated in vacuo (60 torr) at 20° C. followed by evaporation in vacuo (1 torr) at 40° C. to give an oil. This oil was triturated with diethyl ether (50 ml) to give a solid which was filtered and washed with diethyl ether three times. This crude solid was triturated in methanol (100 ml) at reflux temperature three times and the solvent was evaporated to yield $N^6$-benzoyl-9-(β-D-arabinofuranosyladenine)adenine as a solid (1.50 g, 100%).

C. $N^6$-Benzoyl-9-[3",5"-di-) -tetrahydropyran-2-yl)-D-arabinofuranosyl] adenine.

$N^6$-benzoyl-9-(β-D-arabinofuranosyl)adenine (2.62 g, 7.06 m.mol) was dissolved in anhydrous dimethylformamide (150 ml) under an argon atmosphere and p-toluenesulfonic acid monohydrate (1.32 g, 6.92 m.mol) was added. This solution was cooled to ice temperature and dihydropyran (1.26 ml, 13.8 m.mol) was added via syringe. The reaction mixture was allowed to warm to 20° C. Over a period of 5 hours a total of 10 equivalents of dihydropyran were added in 2 equivalent amounts in the fashion described. The reaction mixture was cooled to ice temperature and saturated aqueous sodium bicarbonate was added slowly to a pH of 8, then water was added to a volume of 750 ml. The aqueous mixture was extracted with methylene chloride four times (4×200 ml), and the organic phases were combined and dried over magnesium sulfate. The solids were filtered and the solvent was evaporated in vacuo (60 torr) at 30° C. to give a small volume of liquid which was evaporated in vacuo (1 torr) at 40° C. to give an oil. This oil was coevaporated with p-xylene in vacuo at 40° to give an oil which was dissolved in methylene chloride (100 ml). Hexane (200 ml) was added to the solution and the lower-boiling solvent was evaporated in vacuo at 30° C. to leave a white solid suspended in hexane. This solid was filtered and washed with hexane three times (3×10 ml) then purified by column chromatography using silica and methylene chloride-methanol (93:7, v/v) as eluent. The first fraction yielded the title compound 3 as a white foam (3.19 g, 83%) and a second fraction gave a white foam (0.81 g) which was characterized as the 5'-mono-tetrahydropyranyl derivative of $N^6$-benzoyl-9-(β-D-arabinofuranosyl)adenine.

D. $N^6$-Benzoyl-9-[2'-O-trifluoromethylsulfonyl-3',5'-di-O-(tetrahydropyran-2-yl)-β-D-arabinofuranosyl]adenine.

$N^6$-Benzoyl-9-[3',5'-di-O-(tetrahydropyran-2-yl)-β-D-arabinofuranosyl]adenine (2.65 g, 4.91 m.mol) was dissolved in anhydrous pyridine (20 ml) and the solvent was evaporated in vacuo (1 mm Hg) at 40° C. The resulting oil was dissolved in anhydrous methylene chloride (130 ml) under an argon atmosphere and anhydrous pyridine (3.34 ml, 41.3 m.mol) and N,N-dimethylaminopyridine (1.95 g, 16.0 mmol) were added. The reaction mixture was cooled to ice temperature and trifluoromethanesulfonic anhydride (1.36 ml, 8.05 mmol) was added slowly via syringe. After stirring the reaction mixture at ice temperature for 1 h, it was poured into cold saturated aqueous sodium bicarbonate (140 ml). The mixture was shaken and the organic phase was separated and kept at ice temperature. The aqueous phase was extracted with methylene chloride two more times (2×140 ml). The organic extracts which were diligently kept cold were combined and dried over magnesium sulfate. The solvent was evaporated in vacuo (60 torr) at 20° C. then evaporated in vacuo (1 torr) at 20° C. to give $N^6$-Benzoyl-9-[2'-O-trifluoromethylsulfonyl-3',5'-di-O-(tetrahydropyran-2-yl)-β-arabinofuranosyl]adenine as a crude oil which was not purified further.

E. $N^6$-Benzoyl-9-[2'-fluoro-3',5'-di-O-(tetrahydropyran-2-yl)-β-D-arabinofuranosyl]adenine.

N-Benzoyl-9-[2'-O-trifluoromethylsulfonyl-3',5'-di-O-(tetrahydropyran-2-yl)-β-D-arabinofuranosyl)adenine (<4.9 mmol) as a crude oil was dissolved in anhydrous tetrahydrofuran (120 ml) and this solution was cooled to ice temperature under an argon atmosphere. Tetrabutylammonium fluoride as the hydrate (12.8 g, 49.1 mmol) was dissolved in anhydrous tetrahydrofuran (50 ml) and half of this volume was slowly added via syringe to the cold reaction mixture. After stirring at ice temperature for 1 hour, the remainder of the reagent was added slowly. The reaction mixture was stirred at ice temperature for an additional 1 hour, then the solvent was evaporated in vacuo (60 torr) at 20° C. to give an oil. This oil was dissolved in methylene chloride (250 ml) and washed with brine three times. The organic phase was separated and dried over magnesium sulfate. The solids were filtered and the solvent was evaporated to give an oil. The crude product was purified by column chromatography using silica in a sintered-glass funnel (600 ml) and ethyl acetate was used as eluent. $N^6$-Benzoyl-9-[2'-deoxy-2'-fluoro-3',5'-di-O-(tetrahydropyran-2-yl)-β-D-arabinofuranosyl]adenine was obtained as an oil (2.03 g, 76%).

F. $N^6$-Benzoyl-9-(2'-deoxy-2'-fluoro-β-D-ribofuranosyl) adenine.

$N^6$-Benzoyl-9-[2'-fluoro-3',5'-di-O-tetrahydropyran-2-yl)-β-D-arabinofuranosyl]adenine (1.31 g, 2.42 mmol) was dissolved in methanol (60 ml), and Dowex 50W×2–100 (4 cm3, 2.4 m.eq) was added to the reaction mixture. The reaction mixture was stirred at 20° C. for 1 hour then cooled to ice temperature. Triethylamine (5 ml) was then slowly added to the cold reaction mixture to a pH of 12. The resin was filtered and washed with 30% triethylamine in methanol until the wash no longer contained UV absorbing material. Toluene (50 ml) was added to the washes and the solvent was evaporated at 24° C. in vacuo (60 torr then 1 torr) to give a residue. This residue was partially dissolved in methylene chloride (30 ml) and the solvent was transferred to a separatory funnel. The remainder of the residue was dissolved in hot (60° C.) water and after cooling the solvent it was also added to the separatory funnel. The biphasic system was extracted, and the organic phase was separated and extracted three times with water (3×100 ml). The combined aqueous extracts were evaporated in vacuo (60 torr then 1 torr Hg) at 40° C. to give an oil which was evaporated with anhydrous pyridine (50 ml). This oil was further dried in vacuo (1 torr Hg) at 20° C. in the presence of phosphorous pentoxide overnight to give $N^6$-benzoyl-9-(2'-deoxy-2'-fluoro-β-D-ribofuranosyl)adenine as a yellow foam (1.08 g, 100%) which contained minor impurities.

G. $N^6$-benzoyl-9-[2'-fluoro-5'-O-(4,4'-dimethoxytrityl)-β-D-ribofuranosyl]adenine.

$N^6$-benzoyl-9-(2'-fluoro-b-D-ribofuranosyl)adenine (1.08 g, 2.89 mmol) which contained minor impurities was dissolved in anhydrous pyridine (20 ml) under an argon atmosphere, and dry triethylamine (0.52 ml, 3.76 mmol) was added followed by addition of 4,4'-dimethoxytrityl chloride (1.13 g, 3.32 mmol). After 4 hours of stirring at 20° C. the reaction mixture was transferred to a separatory funnel and diethyl ether (40 ml) was added to give a white suspension. This mixture was washed with water three times (3×10 ml), the organic phase was separated and dried over magnesium sulfate. Triethylamine (1 ml) was added to the solution and the solvent was evaporated in vacuo (60 torr Hg) at 20° C. to give an oil which was evaporated with toluene (20 ml) containing triethylamine (1 ml). This crude product was purified by column chromatography using silica and ethylacetate-triethylamine (99:1, v/v) followed by ethyl acetate-methanol-triethylamine (80:19:1) to give the product in two fractions. The fractions were evaporated in vacuo (60 torr then 1 torr Hg) at 20° C. to give a foam which was further dried in vacuo (1 torr Hg) at 20° C. in the presence of sodium hydroxide to give $N^6$-benzoyl-9-[2'-fluoro-5'-O-(4,4'-dimethoxytrityl)-β-D-ribofuranosyl]adenine as a foam (1.02 g, 52%).

H. $N^6$-Benzoyl-[2'-fluoro-5'-O-(4,4'-dimethoxytrityl)]adenosine-3'-O-N,N-diisopropyl-β-cyanoethyl phosphoramidite.

$N^6$-Benzoyl-9-[2'-fluoro-5'-O-(4,4'-dimethoxytrityl)-β-D-ribofuranosyl)adenine (1.26 g, 1.89 mmol) was dissolved in anhydrous dichloromethane (13 ml) under an argon atmosphere, diisopropylethylamine (0.82 ml, 4.66 mmol) was added, and the reaction mixture was cooled to ice temperature. Chloro(diisopropylamino)-β-cyanoethoxyphosphine (0.88 ml, 4.03 mmol) was added to the reaction mixture which was allowed to warm to 20° C. and stirred for 3 hours. Ethyl acetate (80 ml) and triethylamine (1 ml) were added and this solution was washed with brine solution three times (3×25 ml). The organic phase was separated and dried over magnesium sulfate. After filtration of the solids the solvent was evaporated in vacuo at 20° C. to give an oil which was purified by column chromatography using silica and hexane-ethyl acetate-triethyl-amine (50:49:1) as eluent. Evaporation of the fractions in vacuo at 20° C. gave a foam which was evaporated with anhydrous pyridine (20 ml) in vacuo (1 torr) at 26° C. and further dried in vacuo (1 torr Hg) at 20° C. in the presence of sodium hydroxide for 24 h to give $N^6$-benzoyl-[2'-deoxy-2'-fluoro-5'-O-(4,4'-dimethoxytrityl)]adenosine-3'-O-(N,N-diisopropyl-β-cyanoethylphosphoramidite as a foam (1.05 g, 63%).

I. 2'-Deoxy-2'-fluoro-5'-O-(4,4'-dimethoxytrityl)-uridine-3'-O-(N,N-diisopropyl-β-cyanoethylpbosphoramidite).

2,2'-Cylouridine is treated with a solution of 70% hydrogen fluoride/pyridine in dioxane at 120° C. for ten hours to provide after solvent removal a 75% yield of 2'-deoxy-2'-fluorouridine. The 5'-DMT and 3'-cyanoethoxydiisopropylphosphoramidite derivitized nucleoside is obtained by standard literature procedures, M. J. Gait, ed., *Oligonucleotide Synthesis. A Practical Approach,* (IRL Press, Washington, D.C., 1984) or through the procedure of Example 1A.

J. 2'-Deoxy-2'-fluoro-5'-O-(4,4'-dimethoxytrityl)-cytidine-3'-O-(N,N-diisopropyl-β-cyanoethylphosphoramidite).

2'-Deoxy-2'-fluorouridine is converted to the corresponding cytidine analog via a triazolo intermediate that in turn was aminated The heterocycle is then protected by selective $N^4$-benzoylation. The 5'-O-(4,4'-dimethoxy- trityl)-3'-O-(N,N-diisopropyl-β-cyanoethylphosphoramidite) can be prepared in accordance with Example 1A.

K. 9-(3',5'-[1,1,3,3-Tetraisopropyldisilox-1,3-diyl]-β-D-arabinofuranosyl)guanine.

The 3' and 5' positions of guanosine were protected by the addition of a TPDS (1,1,3,3-tetraisopropyldisilox-1,3-diyl) protecting group as per the procedure of Robins, M. J., Wilson, J. S., Sawyer, L. and James, M. N. G. (1983) *Can. J. Chem.,* 61:1911. To a stirred solution of DMSO (160 mls) and acetic anhydride (20.0 ml, 212 mol) was added the TPDS guanosine (21.0 g, 0.040 mol). The reaction was stirred for 36 hrs at room temperature and then cooled to 0° C. Cold EtOH (400 ml, 95%) was added and the reaction mixture further cooled to −78° C. in a dry ice/acetone bath. $NaBH_4$ (2.0 g, 1.32 mol.eq) was added. The reaction was allowed to come to −2° C., stirred at −2° C. for 30 mins, and again cooled to −78° C. This was repeated twice more. After addition of the $NaBH_4$ was complete, the reaction was stirred at ice temperature for 30 mins and then at RT for 1 hr. The reaction was taken up in EtOAc (11) and washed 2× with a saturated NaCl solution. The organic layer was dried over $MgSO_4$ and evaporated at RT. The residue was co-evaporated 2× with toluene and purified by silica gel column chromatography using $CH_2Cl_2$-MeOH (90:10) as the eluent. 6.02 g of pure product precipitate from the appropriate column fractions during evaporation of these fraction and an additional 11.49 g of product was obtained as a residue upon evaporated of the fractions.

L. $N^2$-Isobutyryl-9-(2'-O-isobutyryl-3',5'-[1,1,3,3-tetraisopropyldisilox-1,3-diyl]-β-D-arabinofuranosyl) guanine.

9-(3',5'-[1,1,3,3-Tetraisopropyldisilox-1,3-diyl]-β-D-arabinofuranosyl)guanine (6.5 g, 0.01248 mol) was dissolved in anhydrous pyridine (156 ml) under argon. DMAP (9.15 g) was added. Isobutyric anhydride (6.12 ml) was slowly added and the reaction mixture stirred at RT overnight. The reaction mixture was poured into cold sat. $NaHCO_3$ (156ml) and stirred for 10 min. The aqueous solution was extracted 3× with EtOAc (156ml). The organic phase was washed 3× with sat. $NaHCO_3$ and evaporated to dryness at RT. The residue was co-evaporated with toluene at RT. The residue was purified by silica gel column chromatography using $CH_2Cl_2$-acetone (85:15) to yield 5.67 g (68%) of product.

M. $N^2$-Isobutyryl-9-(2'-O-isobutyryl-β-D-arabinofuranosyl) guanine.

$N^2$-Isobutyryl-9-(2'-isobutyryl-3',5'-[1,1,3,3-tetraisopropyldisilox-1,3-diyl)-β-D-arabinofuranosyl)

guanine (9.83 g, 0.01476 mol) was dissolved in anhydrous THF (87.4 ml) at RT under argon. 1 M N(nBu)$_4$F in THF (29.52 ml, 2 eq.) was added and the mixture stirred for ½ hr. The reaction mixture was evaporated at RT and the residue purified by silica gel column chromatography using EtOAc-MeOH (85:15) to yield 4.98 g (80%) of product.

N. N$^2$-Isobutyryl-9-(2'-O-isobutyryl-3',5'-di-O-[tetrabydropyran-2-yl]-β-D-arabinofuranosyl)guanine.

N$^2$-Isobutyryl-9-(2'-O-isobutyryl-β-D-arabinofuranosyl) guanine (4.9 g) was dissolved in anhydrous 1,4-dioxane (98 ml) at RT under argon. p-Toluenesulfonic acid monohydrate (0.97 g, 0.44 eq.) was added followed by 3,4-dihydro-2H-pyran, i.e. DHP, (9.34 ml, 8.8 eq.). The mixture was stirred for 2 hrs then cooled to ice temp and sat. NaHCO$_3$ (125 ml) was added to quench the reaction. The reaction mixture was extracted 3× with 125 ml portions of CH$_2$Cl$_2$ and the organic phase dried over MgSO$_4$. The organic phase was evaporated and the residue dissolved in a minimum, but sufficient amount to yield a clear liquid not a syrup, volume of CH$_2$Cl$_2$ and dripped into 100 times the CH$_2$Cl$_2$ volume of hexane. The precipitated was filtered to give 5.59 g (81.5%) of product.

O. N$^2$-Isobutyryl-9-(3',5'-di-O-[tetrabydropyran-2-yl]-β-D-arabinofuranosyl)guanine.

N$^2$-Isobutyryl-9-(2'-O-isobutyryl-3',5'-di-O-[tetrahydropyran-2-yl]-β-D-arabinofuranosyl)guanine (5.58 g) was dissolved in pyridine:MeOH:H$_2$O (65:30:15, 52 ml) at RT. The solution was cooled to ice temp and 52 ml of 2N NaOH in EtOH-MeOH (95:15) was added slowly followed by stirring for 2 hrs at ice temp. Glacial AcOH was added to pH6. Sat. NaHCO$_3$ was then added to pH 7. The mixture was evaporated at RT and the residue co-evaporated with toluene. The residue was dissolved in EtOAc (150 ml) and wash 3× with sat. NaHCO$_3$. The organic phase was evaporated and the residue purified by silica gel column chromatography using EtOAc-MeOH (95:5) to yield 3.85 g (78.3%) of product.

P. N$^2$-Isobutyryl-9-(3=,5'-di-O-[tetrahydropyran-2-yl]-2'-O-trifluormethylsulfonyl-β-D-arabinofuranosyl)guanine.

N$^2$-Isobutyryl-9-(3',5'-di-O-tetrahydropyran-2-yl]-β-D-arabinofuranosyl)guanine (3.84 g) was dissolved in anhydrous CH$_2$Cl$_2$ (79 ml), anhydrous pyridine (5.0 ml) and 4-dimethylaminopyridine (2.93 g) at RT under argon. The solution was cooled to ice temp. and trifluoromethanesulfonic anhydride (1.99 ml) was slowly added with stirring. The mixture was stirred for 1 hr then poured into 100 ml of sat. NaHCO$_3$. The aqueous phase was extracted 3× with cold CH$_2$Cl$_2$. The organic phase was dried over MgSO$_4$, evaporated and co-evaporated with anhydrous CH$_3$CN at RT to yield the crude product.

Q. N$^2$-Isobutyryl-9-(2'-deoxy-2'-fluoro-3',5'-di-O-[tetrahydropyran-2-yl]-β-D-ribofuranosyl)guanine.

The crude product from Example 1-P, i.e. N$^2$-isobutyryl-9-(3',5'-di-O-tetrahydropyran-2-yl]-2'-O-trifluormethylsulfonyl-β-D-arabinofuranosyl)guanine, was dissolved in anhydrous THF (113 ml) under argon at ice temp. 1M anhydrous N(nBu)$_4$F (dried by co-evaporation with pyridine) in THF (36.95 ml) was added with stirring. After 1 hr a further aliquot of 1M N(nBu)$_4$F in THF (36.95 ml) (10 mol. eq. total) was added. The mixture was stirred for 5 hrs at ice temp. and stored in a −30° C. freezer overnight. The reaction mixture was evaporated at RT and the residue dissolved in CH$_2$Cl$_2$ (160 ml) and extracted 5× with deionized H$_2$O. The organic phase was dried over MgSO$_4$ and evaporated. The residue was purified by silica gel column chromatography using EtOAc-MeOH (95:5) to yield 5.25 g of product.

R. N2-Isobutyryl-9-(2'-deoxy-2'-fluoro-β-D-ribofuranosyl) guanine

N$^2$-Isobutyryl-9-(2'-deoxy-2'-fluoro-3',5'-di-O-[tetrahydropyran-2-yl]-β-D-ribofuranosyl)guanine (3.85 g) was dissolved in MeOH (80 ml) at RT. 12.32 cm$^3$ of pre-washed Dowex 50W resin was added and the mixture stirred at RT for 1 hr. The resin was filtered and the filtrate evaporated to dryness. The resin was washed with pyridine-triethylamine-H$_2$O (1:3:3) until clear. This filtrate was evaporated to an oil. The residues from the two filtrates were combined in H$_2$O (200 ml) and washed 3× with CH$_2$Cl$_2$ (100 ml). The aqueous phase was evaporated to dryness and the residue recrystallized from hot MeOH to yield a 0.299 g first crop of product as a white powder. The remaining MeOH solution was purified by silica gel column chromatography yielding a further crop of 0.783 g by elution with EtOH-MeOH (80:20).

S. N$^2$-Isobutyryl-9-(2'-deoxy-2'-fluoro-5'-O-[4,4'-dimetboxytrityl]-β-D-ribofuranosyl)guanine.

N$^2$-Isobutyryl-9-(2'-deoxy-2'-fluoro-β-D-ribofuranosyl) guanine (1.09 g) was dissolved in pyridine (20 ml) and triethylamine (0.56 ml) at RT under argon. 4,4'-Dimethoxytrityl chloride (1.20 g, 1.15 molar eq.) was added and the mixture stirred at RT for 5 hrs. The mixture was transferred to a separatory funnel and extracted with Et$_2$O (100 ml). The organic phase was washed 3× with sat. NaHCO$_3$ (70 ml portions) and the aqueous phase back extracted 3× with Et$_2$O. The combined organic phases were dried over MgSO$_4$ and triethylamine (4 ml) added to maintain the solution basic. The solvent was evaporated and the residue purified by silica gel column chromatography. The column was eluted with EtOAc-Et$_3$N (100:1) and then EtOAc-MeOH-Et$_3$N (95:5:1) to yield 1.03 g of product. $^1$H-NMR (DMSO-d$_6$) δ 6.09 (dd, 1, H1', J$_{1-2}$=2.61, J$_{1',F}$=16.2 Hz); δ 5.28 (ddd, 1, H2', J$_{2',F}$=52.8 Hz); δ 4.38 (m, 1, H3', J$_{3',F}$=19.8 Hz).

T. N$^2$-Isobutyryl-9-(2'-deoxy-2'-fluoro-5'-O-[4,4'-dimethoxytrityl])guanosine-3'-O-N,N-diisopropyl-β-cyanoethyl phosphoramidite.

N$^2$-Isobutyryl-9-(2'-deoxy-2'-fluoro-5'-O-[4,4'-dimethoxytrityl]-β-D-ribofuranosyl)guanine (0.587 g) was dissolved in anhydrous CH$_2$Cl$_2$ (31 ml) and diisopropylethylamine (0.4 ml) at RT under argon. The solution was cooled to ice temp and chloro(diisopropylamino)-β-cyanoethoxyphosphine (0.42 ml) was slowly added. The reaction was allowed to warm to RT and stirred for 3.5 hrs. CH$_2$Cl$_2$-Et$_3$N (100:1, 35 ml) was added and the mixture washed 1× with sat. NaHCO$_3$ (6 ml). The organic phase was dried over MgSO$_4$ and evaporated at RT. The residue was purified by silica gel column chromatography using Hex-EtOAc-Et$_3$N (75:25:1) for 2 column volumes, then Hex-EtOAc-Et$_3$N (25:75:1) and finally EtOAc-Et$_3$N. The product containing fractions were pooled and evaporated at RT. The resulting oil was co-evaporated 2× with CH$_3$CN and placed on a vacuum pump overnight to dry. The resulting white solid was dissolved in CH$_2$Cl$_2$ (3 ml) and dripped into stirring hexane (300 ml). The resulting precipitate was filtered and dried on a vacuum pump to yield 0.673 g (88%) of product. $^{31}$P-NMR (CDCl$_3$) δ 150.5, 151.5.

EXAMPLE 2

Preparation of 2'-Deoxy-2'-cyano Modified Oligonucleotides

A. N$^6$-Benzoyl-[2'-deoxy-2'-cyano-5'-O-(4,4'-dimethoxytrityl)]adenosine-3'-O-(N,N-diisopropyl-β-cyanoethylphosphoralidite).

2'-Deoxy-2'-cyanoadenosine is prepared by the free radical replacement of the 2'-iodo group of 2'-deoxy-2'-iodo-3', 5'-O-(disiloxytetraisopropyl)-N6-benzoyladenosine according to a similar procedure described by K. E. B. Parkes and K. Taylor, *Tetrahedron Letters* 29:2995–2996 (1988). 2'-Deoxy-2'-iodoadenosine was prepared by R. Ranganathan as described in *Tetrahedron Letters* 15:1291–1294 (1977), and disilyated as described by W. T. Markiewicz and M. Wiewiorowski in *Nucleic Acid Chemistry*, Part 3, pp. 222–231, Townsend, L. B.; Tipson, R. S. eds. (J. Wiley and Sons, New York, 1986). This material is treated with hexamethylditin, AIBN, and t-butylisocyanate in toluene to provide protected 2'-deoxy-2'-cyanoadenosine. This material, after selective deprotection, is converted to its 5'-DMT-3'-phosphoramidite as described in Example 1A.

B. 2'-Deoxy-2'-cyano-5'-O-(4,4'-dimethoxytrityl)uridine-3'-O-(N,N-diisopropyl-β-cyanoethyl phosphoramidite).

2'-Deoxyuridine (or 5-methyluridine), 3',5'-disilylated as described above, is converted to the 2'-iodo derivative by triphenylphosphonium methyl iodide treatment as described by K. E. B. Parkes and K. Taylor, *Tetrahedron Letters* 29:2995–2996 (1988). Application of free radical reaction conditions as described by K. E. B. Parkes and K. Taylor, *Tetrahedron Letters* 29:2995–2996 (1988), provides the 2'-cyano group of the protected nucleoside. Deprotection of this material and subsequent conversion to the protected monomer as described above provides the requisite nucleic acid synthesizer material.

C. 2'-Deoxy-2'-cyano-5'-O-(4,4'-dimethoxytrityl)cytidine-3'-O-(N,N-diisopropyl-β-cyanoethyl phosphoramidite).

2'-Deoxy-2'-iodocytidine is obtained from the corresponding above described uridine compound via a conventional keto to amino conversion.

D. 2'-Deoxy-2'-cyano-5'-O-(4,4'-dimethoxytrityl)-guanosine-3'-O-(N,N-diisopropyl-β-cyanoethyl phosphoramidite).

2'-Deoxy-2'-cyanoguanosine is obtained by the displacement of the triflate group in the 2'-up position (arabino sugar) of 3',5'-disilylated N2-isobutrylguanosine. Standard deprotection and subsequent reprotection provides the title monomer.

EXAMPLE 3

Preparation of 2'-Deoxy-2'-(trifluoromethyl) Modified Oligonucleotides

The requisite 2'-deoxy-2'-trifluromethyribosides of nucleic acid bases A, G, U(T), and C are prepared by modifications of a literature procedure described by Q.-Y. Chen and S. W. Wu in the *Journal of Chemical Society Perkin Transactions* 2385–2387 (1989). Standard procedures, as described in Example 1A, are employed to prepare the 5'-DMT and 3'-phosphoramidites as listed below.

A. $N^6$-Benzoyl-[2'-deoxy-2'-trifluoromethyl-5'-O-(4,4'-dimetboxytrityl)]adenosine-3'-O-(N,N-di-isopropyl-β-cyanoethyl phosphoramidite).

B. 2'-Deoxy-2'-trifluorometbyl-5'-O-(4,4'-dimethoxytrityl) uridine-3'-O-(N,N-diisopropyl-β-cyanoethyl-phosphoramidite).

C. 2'-Deoxy-2'-trifluoromethyl-5'-O-(4,4'-dimethoxytrityl) cytidine-3'-O-(N,N-diisopropyl-β-cyanoethyl-phosphoramidite).

D. 2'-Deoxy-2'-trifluoromethyl-5'-O-(4,4'-dimethoxytrityl) guanosine-3'-O-(N,N-diisopropyl-β-cyano-etbylphosphoramidite).

EXAMPLE 4

Preparation of 2'-Deoxy-2'-(trifluoromethoxy) Modified Oligonucleotides

The requisite 2'-deoxy-2'-O-trifluoromethylribosides of nucleic acid bases A, G, U(T), and C are prepared by modifications of literature procedures described by B. S. Sproat, et al., *Nucleic Acids Research* 18:41–49 (1990) and H. Inoue, et al., *Nucleic Acids Research* 15:6131–6148 (1987). Standard procedures, as described in Example 1A, are employed to prepare the 5'-DMT and 3'-phosphoramidites as listed below.

A. N6-Benzoyl-[2'-deoxy-2'-(trifluoromethoxy)-5-O-(4,4'-dimethoxytrityl)]adenosine-3'-O-(N,N-diisopropyl-β-cyanoethylphosphoramidite).

B. 2'-Deoxy-2'-(trifluoromethoxy)-5'-O-(4,4'-dimethoxytrityl)uridine-3'-O-(N,N-diisopropyl-β-cyanoethylphosphoramidite).

C. 2'-Deoxy-2'-(trifluoromethoxy)-5'-O-(4,4'-dimethoxytrityl)cytidine-3'-O-(N,N-diisopropyl-β-cyanoethylphosphoramidite).

D. 2'-Deoxy-2'-(trifluoromethoxy)-5'-O-(4,4'-dimethoxytrityl)guanosine-3'-O-(N,N-diisopropyl-β-cyanoethylphosphoramidite).

EXAMPLE 5

Preparation of 2'-Deoxy-2'-(1-proproxy) Modified Oligonucleotides

The requisite 2'-deoxy-2'-O-propyl ribosides of nucleic acid bases A, G, U(T), and C are prepared by modifications of literature procedures described by B. S. Sproat, et al., *Nucleic Acids Research* 18:41–49 (1990) and H. Inoue, et al., *Nucleic Acids Research* 15:6131–6148 (1987). Standard procedures, as described in Example 1A, are employed to prepare the 5'-DMT and 3'-phosphoramidites as listed below.

A. $N^6$-Benzoyl-[2'-deoxy-2-(1-proproxy)-5'-O-(4,4'-dimethoxytrityl)]adenosine-3'-O-(N,N-diisopropyl-β-cyanoethyl phosphoramidite).

B. 2'-Deoxy-2'-(-proproxy)-5'-O-(4,4'-dimethoxytrityl) uridine-3'-O-(N,N-diisopropyl-β-cyanoethylphosphoramidite).

C. 2'-Deoxy-2'-(1-proproxy)-5'-O-(4,4'-dimethoxytrityl) cytidine-3'-O-(N,N-diisopropyl-β-cyanoethylphosphoramidite).

D. 2'-Deoxy-2'-(1-proproxy)-5'-O-(4,4'-dimethoxytrityl) guanosine-3'-O-(N,N-diisopropyl-β-cyanoethylphosphoramidite).

EXAMPLE 6

Preparation of 2'-Deoxy-2'-(vinyloxy) Modified Oligonucleotides.

The requisite 2'-deoxy-2'-O-vinyl ribosides of nucleic acid bases A, G, U(T), and C are prepared by modifications of literature procedures described by B. S. Sproat, et al., *Nucleic Acids Research* 18:41–49 (1990) and H. Inoue, et al., *Nucleic Acids Research* 15:6131–6148 (1987). In this case 1,2-dibromoethane is coupled to the 2'-hydroxyl and subsequent dehydrobromination affords the desired blocked 2'-vinyl nucleoside. Standard procedures, as described in Example 1A, are employed to prepare the 5'-DMT and 3'-phosphoramidites as listed below.

A. $N^6$-Benzoyl-[2'-deoxy-2'-(vinyloxy)-5'-O-(4,4'-dimethoxytrityl)]adenosine-3'-O-(N,N-diisopropyl-β-cyanoethylphosphoramidite).

B. 2'-Deoxy-2'-(vinyloxy)-5'-O-(4,4'-dimethoxytrityl) uridine-3'-O-(N,N-diisopropyl-β-cyanoethylphosphoramidite).

C. 2'-Deoxy-2'-(vinyloxy)-5'-O-(4,4'-dimethoxytrityl) cytidine-3'-O-(N,N-diisopropyl-β-cyanoethylphosphoramidite).

D. 2'-Deoxy-2'-(vinyloxy)-5'-O-(4,4'-dimethoxytrityl) guanosine-3'-O-(N,N-diisopropyl-β-cyanoethylphosphoramidite).

EXAMPLE 7

Preparation of 2'-Deoxy-2'-(allyloxy) Modified Oligonucleotides

The requisite 2'-deoxy-2'-O-allyl ribosides of nucleic acid bases A, G, U(T), and C are prepared by modifications of literature procedures described by B. S. Sproat, et al., *Nucleic Acids Research* 18:41–49 (1990) and H. Inoue, et al., *Nucleic Acids Research* 15:6131–6148 (1987). Standard procedures, as described in Example 1A, are employed to prepare the 5'-DMT and 3'-phosphoramidites as listed below.

A. $N^6$-Benzoyl-[2'-deoxy-2'-(allyloxy)-5'-O-(4,4'-dimethoxytrityl)]adenosine-3'-O-(N,N-diisopropyl-β-cyanoethylphosphoramidite).

B. 2'-Deoxy-2'-(allyloxy)-5'-O-(4,4'-dimethoxytrityl)-uridine-3'-O-(N,N-diisopropyl-β-cyanoethylphosphoramidite).

C. 2'-Deoxy-2'-(allyloxy)-5'-O-(4,4'-dimethoxytrityl)-cytidine-3'-O-(N,N-diisopropyl-β-cyanoethylphosphoramidite).

D. 2'-Deoxy-2'-(allyloxy)-5'-O-(4,4'-dimethoxytrityl)-guanosine-3'-O-(N,N-diisopropyl-β-cyanoethylphosphoramidite).

EXAMPLE 8

Preparation of 2'-Deoxy-2'-(methylthio), (methylsulfinyl) and (methylsulfonyl) Modified Oligonucleotides A. 2'-Deoxy-2'-Methylthiouridine 2,2'-Anhydrouridine (15.5 g, 68.2 mmol) [Rao, T. S. and Reese, C. B. (1989) *J. Chem. Soc., Chem. Commun.*, 997], methanethiol (15.7 g, 327 mmol), 1,1,3,3-tetramethylguanidine (39.2 g, 341 mmol) and dimethylforamide (150 ml) were heated together at 60° C. After 12 hr, the reaction mixture was cooled and concentrated under reduced pressure. The residual oil was purified by flash column chromatography on silica gel (300 g). Concentration of the appropriate fractions, which were eluted with $CH_2Cl_2$-MeOH (9:1, v/v), and drying of the residue under high vacuum gave 2'-deoxy-2'-methylthiouridine as a pale yellow solid (14.11 g, 75.4%). Attempts to crystallize the solids from ethanol-hexanes (as reported by Imazawa, M., Ueda, T., and Ukita, T. (1975) *Chem. Pharm. Bull.*, 23:604) failed and the material turned into a hygroscopic foam.

$^1$H NMR ($Me_2SO$-$d_6$) δ 2.0 (3H, s, $SCH_3$), 3.34 (1H, dd, $J_{3',2'}$=54.Hz, 2'$\underline{H}$), 3.59 (2H, br m, 5'$C\underline{H}_2$), 3.84 (1H, m, 4'$\underline{H}$), 4.2 (1H, dd, $J_{3',4'}$=2.2 Hz, 3'$\underline{H}$), 5.15 (1H, t, 5'O$\underline{H}$), 5.62 (1H, t, 3'O$\underline{H}$), 5.64 (1H, d, $J_{C6,C5}$=8.2 Hz), 6.02 (1H, d, $J_{1',2'}$=6 Hz, 1'$\underline{H}$), 7.82 (1H, d, $J_{C5,C6}$=8.2 Hz, $C_6\underline{H}$), 11.38 (1H, br s, N$\underline{H}$).

B. 2,2'-Anhydro-5-Methyluridine

A mixture of 5-methyluridine (16.77 g, 69.2 mmol), diphenyl carbonate (17.8 g, 83.1 mmol) and sodium bicarbonate (100 mg) in hexamethylphosphoramide (175 ml) was heated to 150° C. with stirring until evolution of $CO_2$ ceased (approximately 1 hr). The reaction mixture was cooled and then poured into diethylether (1 l) while stirring to furnish a brown gum. Repeated washings with diethylether (4×250 ml) furnished a straw colored hygroscopic powder. The solid was purified by short column chromatography on silica gel (400 g). Pooling and concentration of appropriate fractions, which were eluted with $CH_2Cl_2$-MeOH (85:15, v/v) furnished the title compound as a straw colored solid (12 g, 77.3%) which crystallized from EtOH as long needles, m.p. 226–227° C.

C. 2'-Deoxy-2'-Methylthio-5-Methyluridine 2.2'-Anhydro-5-methyluridine (17.02 g, 70.6 mmol), methanethiol (16.3 g, 339 mmol), 1,1,3,3-tetramethylguanidine (40.6 g, 353 mmol), and dimethylformamide (150 ml) were heated together at 60° C. After 12 hr, the products were cooled and concentrated under reduced pressure. The residual oil was purified by short silica gel (300 g) column chromatography. Concentration of appropriate fractions, which were eluted with $CH_2Cl_2$-MeOH (93:7, v/v), furnished the title compound as a white foam (15.08 g, 74.1%). Crystallization from EtOH-$CH_2Cl_2$ furnished white needles.

D. 2'-Deoxy-2'-Methylsulfinyluridine

To a stirred solution of 2'-deoxy-2'methylthiouridine (1 g, 3.65 mmol) in EtOH (50 ml) was added a solution of m-chloroperbenzoic acid (50%, 1.26 g, 3.65 mmol in 50 ml EtOH) over a period of 45 min at 0° C. The solvent was removed under vacuum and the residue purified by short silica gel (30 g) column chromatography. Concentration of appropriate fractions, which were eluted with $CH_2Cl_2$-MeOH (75:25, v/v), afforded the title compound as a white solid (0.65 g, 61.4%). Crystallization from EtOH furnished white granules, m.p. 219–221° C.

$^1$H NMR ($Me_2SO$-$d_6$) δ 2.5(3H, s, $SOCH_3$), 3.56 (2H, br s, 5'$C\underline{H}_2$), 3.8 (1H, m, 4'$\underline{H}$), 3.91 (1H, m, 2'$\underline{H}$), 4.57 (1H, m, 3'$\underline{H}$), 5.2 (1H, br s, 5'O$\underline{H}$), 5.75 (1H, d, $C_5\underline{H}$), 6.19 (1H, d, 3'O$\underline{H}$), 6.35 (1H, d, 1'$\underline{H}$), 7.88 (1H, d, $C_6\underline{H}$), 11.43 (1H, br s, N$\underline{H}$).

E. 2'-Deoxy-2'-Methylsulfonyluridine

To a stirred solution of 2'-deoxy-2'-methyluridine (1 g, 3.65 mmol) in EtOH (50 ml) was added m-chloroperbenzoic acid (50%, 3.27 g, 14.6 mmol) in one portion at room temperature. After 2hr., the solution was filtered to collect a white precipitate, which on washing (2×20 ml, EtOH and 2×20 ml $Et_2O$) and drying furnished the title compound as a fine powder (0.76 g, 68%), m.p. 227–228° C.

$^1$H NMR ($Me_2SO$-$d_6$) δ 3.1 (3H, s, $SO_2CH_3$), 3.58 (2H, m, 5'$C\underline{H}_2$), 3.95 (1H, m, 2'H), 3.98 (1H, m, 4'$\underline{H}$), 4.5 (1H, br s, 3'$\underline{H}$), 5.2 (1H, br s, 5'O$\underline{H}$), 5.75 (1H, d, $C_5\underline{H}$), 6.25 (1H, d, 3'O$\underline{H}$), 6.5 (1H, d, 1'H), 7.8 (1H, d, $C_6\underline{H}$), 11.45 (1H, br s, N$\underline{H}$).

F. 2'-Deoxy-5-O-(4,4'-Dimethoxytrityl)-2'-Methylthiouridine

To a stirred solution of 2'-deoxy-2'-methylthiouridine (1.09 g, 4 mmol)) in dry pyridine (10 ml) was added 4,4'-dimethoxytritylchloride (1.69 g, 5 mmol) and 4-dimethylaminopyridine (50 mg) at room temperature. The solution was stirred for 12 hr and the reaction quenched by adding MeOH (1 ml). The reaction mixture was concentrated under vacuum and the residue dissolved in $CH_2Cl_2$ (100 ml), washed with sat. aq. $NaHCO_3$ (2×50 ml), sat. aq. NaCl (2×50 ml), and dried ($MgSO_4$). The solution was concentrated under vacuum and the residue purified by silica gel (30 g) column chromatography. Elution with $CH_2Cl_2$-MeOH:triethylamine (89:1:1, v/v) furnished the title compound as homogenous material. Pooling and concentration of appropriate fractions furnished the 5'-O-DMT nucleoside as a foam (1.5 g, 66.5%).

$^1$H NMR ($MeSO$-$d_6$) δ 2.02 (3H, S, $SCH_3$), 3.15–3.55 (1H, m, 2'$C\underline{H}$), 3.75 (6H, s, 2 $OCH_3$), 3.97 (1H, m, 4'$\underline{H}$), 4.24 (1H, m, 3'$\underline{H}$), 5.48 (1H, d, $C_5\underline{H}$), 5.73 (1H, d, 3'-O$\underline{H}$), 6.03 (1H, d, C1'$\underline{H}$), 6.82–7.4 (13H, m, Ar$\underline{H}$), 6.65 (1H, d, $C_6H$), 11.4 (1H, br s, N$\underline{H}$).

G. 2'-Deoxy-3'-O-[(N,N-diisopropyl)-O-β-cyanoethylphosphoramide]-5'-O-(4,4'-dimethoxytrityl)-2'-Methylthiouridine To a stirred solution of 2'-deoxy-5'-O-(4,4'-dimethoxytrityl)-2'-methylthiouridine (1.5 g, 2.67 mmol) in dry THF (25 ml) was added diisopropylethylamine (1.4 ml, 8 mmol) and the solution cooled to 0° C. N,N-diisopropyl-β-cyanoethylphosphoramidic chloride (1.26 ml, 5.34 mmol) was added dropwise over a period of 15 min. The reaction mixture was then stirred at room temperature for 2 hr. EtOAc (100 ml, containing 1% triethylamine) was added and the solution washed with sat NaCl (2×50 ml) and the organic layer dried over $MgSO_4$. The solvent was removed under pressure and the residue purified by short silica gel (30 g) column chromatography. Elution with $CH_2Cl_2$:MeOH:triethylamine (98:1:1, v/v) furnished the product as a mixture of diastereoisomers. Evaporation of the appropriate fractions provided the title compound as a foam (1.32 g, 64.7%).

$^1H$ NMR ($CDCl_3$) δ 2.0 and 2.02 (3H, 2s, $SCH_3$), 5.3 and 5.35 (1H, 2d, $C_5H$), 6.23 (1H, d, 1'$H$), 7.8 and 7.78 (1H, 2d, $C_6H$) and other protons. $^{31}P$ NMR ($CDCl_3$) δ 151.68 and 152.2 ppm.

H. 2'-Deoxy-3',5'-di-O-Acetyl-2'-Methylthiouridine

2'-Deoxy-2'-methylthiouridine (5.0 g, 18.24 mmol) and acetic anhydride (5.6 ml, 54.74 mmol) were stirred together in dry pyridine (30 ml) at room temperature for 12 hr. The products were then concentrated under reduced pressure and the residue obtained was purified by short silica gel column chromatography. The appropriate fractions, which were eluted with $CH_2Cl_2$:MeOH (9:1, v/v), were combined, evaporated under reduced pressure and the residue was crystallized from EtOH to give the title compound (6.0 g, 91.8%) as white needles, m.p. 132° C.

$^1H$ NMR ($CDCl_3$) δ 2.17 (3H, s, $SCH_3$), 2.20 (6H, s, 2 $COCH_3$), 3.40 (1H, t, 2'$H$), 4.31–4.40 (3H, m, 4',5'$H$), 5.31 (1H, m, 3'$H$), 5.80 (1H, d, $C_5H$), 6.11 (1H, d, 1'H), 7.45 (1H, d, $C_6H$), 8.7 (1H, br s, N$H$).

I. 2'-Deoxy-3',5'-di-O-Acetyl-4-(1,2,4-triazol-1-yl)-2'-Methylthiouridine

Triethylamine (8.4 ml, 60.3 mmol) and phosphoryl chloride (1.2 ml, 12.9 mmol) were added to a stirred solution of 2'-deoxy-3',5'-di-O-acetyl-2'-methylthiouridine (4.6 g, 13 mmol) in $CH_3CN$ (50 ml). 1,2,4-Triazole (4.14 g, 59.9 mmol) was then added and the reactants were stirred together at room temperature. After 16 hr, triethylamine-water (6:1, v/v; 20 ml) followed by sat. aq. $NaHCO_3$ (100 ml) were added to the products and the resulting mixture was extracted with $CH_2Cl_2$ (2×100 ml). The organic layer was dried ($MgSO_4$) and evaporated under reduced pressure. The residue was purified by short silica gel column chromatography. The appropriate fractions, which were eluted with $CH_2Cl_2$:MeOH (9:1, v/v), were evaporated under vacuum and the residue was crystallized from EtOH to give the title compound (3.01 g, 56.4%) as pale needles, m.p. 127–130° C.

$^1H$ NMR ($CDCl_3$) δ 2.18 (6H, s, 2 $COCH_3$), 2.30 (3H, s, $SCH_3$), 3.67 (1H, m, 2'$H$), 4.38–4.50 (3H, m, 4',5'$H$), 5.17 (1H, t, 3'$H$), 6.21 (1H, d, 1'$H$), 7.08 (1H, d, $C_5H$), 8.16 (1H,s, C$H$), 8.33 (1H, d, $C_6H$), 9.25 (1H, s, C$H$).

J. 2'-Deoxy-2'-Methylthiocytidine

2'-Deoxy-3',5'-di-O-acetyl-4-(1,2,4-triazol-1-yl)-2'-methylthiouridine (3.0 g, 7.5 mmol) was dissolved in a saturated solution of ammonia in MeOH (70 ml) and the solution was stirred at room temperature in a pressure bottle for 3 days. The products were then concentrated under reduced pressure and the residue was crystallized from EtOH:$CH_2Cl_2$ to give the title compound (1.06 g, 51.7%) as crystals, m.p. 201° C.

$^1H$ NMR ($Me_2SO$-$d_6$) δ 1.95 (3H, s, $SCH_3$), 3.36 (1H, m, 2'$H$), 3.55 (2H, m, 5'$CH_2$), 3.82 (1H, m, 4'$H$), 4.18 (1H, dd, 3'$H$), 5.75 (1H, d, $C_5H$), 6.1 (1H, d, 1'$H$), 7.77 (1H, d, $C_6H$).

Anal. calcd. for $C_{10}H_{15}N_3O_4S$: C, 43.94; H, 5.53; N, 15.37; S, 11.73. Found, C, 44.07; H, 5.45; N, 15.47; S, 11.80.

K. 2'-Deoxy-$N^4$-Benzoyl-2'-Methylthiocytidine

To a stirred solution of 2'-deoxy-2'-methylthiocytidine (0.86 g, 3.15 mmol) in dry pyridine (20 ml) was added trimethylchlorosilane (2.0 ml, 15.75 mmol), and stirring continued for 15 min. Benzoyl chloride (2.18 ml, 18.9 mmol) was added to the solution followed by stirring for 2 hr. The mixture was then cooled in an ice-bath and MeOH (10 ml) was added. After 5 mins., $NH_4OH$ (20 ml, 30% aq.) was added and the mixture stirred for 30 min. The reaction mixture was then concentrated under vacuum and the residue purified by short silica gel (70 g) column chromatography. Elution with $CH_2Cl_2$:MeOH (9:1, v/v), pooling of appropriate fractions and evaporation furnished the title compound (0.55 g, 46.6%) which crystallized from EtOH as needles, m.p. 193–194° C.

L. $N^4$-Benzoylamino-1-[2-Deoxy-5-(4,4'-Dimethoxytrityl)-2-Methylthio-β-D-Ribofuranosyl]pyrimidin-3(2H)-one (or 2'-Deoxy-$N^4$-Benzoyl-5'-(4,4'-Dimethoxytrityl)-2'-Methylthiocytidine)

To a stirred solution of 2'-deoxy-$N^4$-benzoyl-2'-methylthiocytidine (0.80 g, 2.12 mmol) in dry pyridine (10 ml) was added 4,4'-dimethoxytrityl chloride (1.16 g, 3.41 mmol) and 4-dimethylaminopyridine (10 mg) at room temperature. The solution was stirred for 2 hr and the products concentrated under vacuum. The residue was dissolved in $CH_2Cl_2$ (70 ml), washed with sat. $NaHCO_3$ (50 ml), sat. NaCl (2×50 ml), dried ($MgSO_4$) and evaporated under reduced pressure. The residue was purified by short silica gel (50 g) column chromatography. Elution with $CH_2Cl_2$:triethylamine (99:1, v/v), pooling and concentration of appropriate fractions furnished the title compound (1.29 g, 90%) as a white foam.

$^1H$ NMR (DMSO-$d_6$) δ 2.1 (3H, s, $SCH_3$), 3.5 (1H, m, 2'$H$), 3.75 (6H, s, $OCH_3$), 4.15 (1H, m, 4'$H$), 4.4 (1H, t, 3'$H$), 5.74 (1H, br d, 3'O$H$), 6.15 (1H, d, C1'$H$), 6.8–8.0 (25H, m, Ar$H$, and $C_5H$), 8.24 (1H, d, $C_6H$), 11.3 (1H, br s, N$H$).

M. 2'-Deoxy-$N^4$-Benzoyl-3-O-[(N,N-Diisopropyl)-β-Cyanoethylphosphoramide]-5'-O'-(4,4'-Dimethoxytrityl)-2'-Methylthiocytidine 2'-Deoxy-$N^4$-benzoyl-5'-(4,4'-dimethoxytrityl)-2'-methylthiocytidine (1.41 g, 2.07 mmol) was treated with diisopropylethylamine (1.4 ml, 8 mmol) and N,N-diisopropyl-β-cyanoethylphophoramide chloride (1.26 ml, 5.34 mmol) in dry THF (25 ml) as described in Example 8-G above. The crude product was purified by short silica gel (50 g) chromatography to furnish the title compound on elution with $CH_2Cl_2$:hexanes:triethylamine (89:10:1, v/v). The appropriate fractions were mixed and evaporated under pressure to give the title compound (1.30 g, 71%) as a white foam (mixture of diastereoisomers).

$^1H$ NMR ($CDCl_3$) δ 2.31 (3H, s, $SCH_3$), 3.45–3.7 (3H, m, 2'$H$ and 5'$CH_2$), 3.83 (6H, s, $OCH_3$), 4.27–4.35 (1H, m, 4' $H$), 4.6–4.8 (1H, m, 3'$H$), 6.35 (1H, 2d, 1'$H$), 6.82–7.8 (25H, m, Ar$H$ and $C_5H$), 8.38 and 8.45 (1H, 2d, $C_6H$) and other protons. $^{31}P$ NMR δ 151.03 and 151.08 ppm.

N. 2'-Deoxy-2'-Methylsulfinylcytidine

2'-Deoxy-2'-methylthiocytidine of Example 8-J was treated as per the procedure of Example 8-D to yield the title compound as a mixture of diastereoisomers having a complex $^1H$ NMR spectrum.

O. 2'-Deoxy-2'-Methylsulfonylcytidine

2'-Deoxy-2'-methylthiocytidine of Example 8-J was treated as per the procedure of Example 8-E to yield the title compound.

P. $N^6$-Benzoyl-3',5'-di-O-[Tetrabydropyran-2-yl]-2'-Deoxy-2'-Methylthioadenosine $N^6$-Benzoyl-9-2'-O-trifluoromethylsulfonyl-3',5'-di-O-(tetrahydropyran-2-yl)-β-D-arabinofuranosyl]adenine from Example 1-D is prepared by treatment with methanethiol in the presence of tetramethylguanidine to yield the title compound.

Q. $N^6$-Benzoyl-2'-Deoxy-2'-Methylthioadenosine $N^6$-Benzoyl-3',5'-di-O-(tetrahydropyran-2-yl)-2'-deoxy-2'-methylthioadenosine from Example 8-P is treated as per Example 1-F to yield the title compound.

R. $N^6$-Benzoyl-2'-Deoxy-2'-Methylsulfinyladenosine $N^6$-Benzoyl-2'-deoxy-2'-methylthioadenosine from Example 8-Q was treated as per the procedure of Example 8-D to yield the title compound.

S. $N^6$-Benzoyl-2'-Deoxy-2'-Methylsulfonyladenosine $N^6$-Benzoyl-2'-deoxy-2'-methylthioadenosine from Example 8-Q was treated as per the procedure of Example 8-E to yield the title compound.

T. $N^2$-Isobutyryl-3',5'-di-O-(tetrabydropyran-2-yl)-2'-Deoxy-2'-Methylthioguanosine $N^2$-Isobutyryl-9-(3',5'-di-O-[tetrahydropyran-2-yl]-2'-O-trifluoromethylsulfonyl-β-D-arabinofuranosyl)guanine from Example 1-P is treated with methanethiol in the presence of 1,1,3,3-tetramethylguanidine to yield the title compound.

U. $N^2$-Isobutyryl-2'-Deoxy-2'-Methylthioguanosine $N^2$-Isobutyryl-3',5'-di-O-(tetrahydropyran-2-yl)-2'-deoxy-2'-methylthioguanosine is treated as per Example 1-R to yield the title compound.

V. $N^2$-Isobutyryl-2'-Deoxy-2'-Methylsulfinylguanosine $N^2$-Isobutyryl-2'-Deoxy-2'-methylthioguanosine from Example 8-U was treated as per the procedure of Example 8-D to yield the title compound.

W. N2-Isobutyryl-2'-Deoxy-2'-Methylsulfonylguanosine $N^2$-Isobutyryl-2'-Deoxy-2'-methylthioguanosine from Example 8-U was treated as per the procedure of Example 8-E to yield the title compound.

X. 2'-Deoxy-5-O-(4,4'-Dimethoxytrityl)-2'-Methylsulfinyluridine

2'-Deoxy-2'-methylsulfinyluridine from Example 8-D above is treated as per Example 8-F to yield the title compound.

Y. 2'-Deoxy-3'-O-[(N,N-Diisopropyl)-O-β-cyanoethylphosphoramide]-5'-O-(4,4'-Dimethoxytrityl)-2'-Methylsulfinyluridine 2'-Deoxy-5'-O-(4,4'-dimethoxytrityl)-2'-methylsulfinyluridine is treated as per Example 8-G to yield the title compound.

Z. $N^6$-Benzoyl-2'-Deoxy-5-O-(4,4'-Dimethoxytrityl)-2'-Methylthioadenosine $N^6$-benzoyl-2'-Deoxy-2'-methylthioadenosine from Example 8-Q above is treated as per Example 8-F to yield the title compound.

AA. $N^6$-Benzoyl-2'-Deoxy-3'-O-[(N,N-Diisopropyl)-O-β-Cyanoetbylphosphoramide]-5'-O-(4,4'-Dimethoxytrityl)-2'-Metbylthioadenosine $N^6$-benzoyl-2'-Deoxy-5'-O-(4,4'-dimethoxytrityl)-2'-methylthioadenosine is treated as per Example 8-G to yield the title compound.

BB. 2'-Deoxy-$N^2$-Isobutyryl-5-O-(4,4'-Dimethoxytrityl)-2'-Methylthioguanosine

2'-Deoxy-$N^2$-isobutyryl-2'-methylthioguanosine from Example 8-U above is treated as per Example 8-F to yield the title compound.

CC. 2'-Deoxy-$N^2$-Isobutyryl-3'-O-[(N,N-Diisopropyl)-O-β-Cyanoethylphosphoramide]-5'-O-(4,4'-Dimethoxytrityl)-2'-Methylthioguanosine 2'-Deoxy-$N^2$-isobutyryl-5'-O-(4,4'-dimethoxytrityl)-2'-methylthioguanosine is treated as per Example 8-G to yield the title compound.

DD. 2'-Deoxy-5-O-(4,4'-Dimethoxytrityl)-2'-Methylsulfonyluridine

2'-Deoxy-2'-methylsulfonyluridine from Example 8-E above is treated as per Example 8-F to yield the title compound.

EE. 2'-Deoxy-3'-O-[(N,N-Diisopropyl)-O-β-Cyanoethylphosphoramide]-5'-O-(4,4'-Dimethoxytrityl)-2'-Methylsulfinyluridine 2'-Deoxy-5'-O-(4,4'-dimethoxytrityl)-2'-methylsulfinyluridine is treated as per Example 8-G to yield the title compound.

EXAMPLE 9

Chemical Conversion of an Thymine or Cytosine (Pyrimidine Type Base) to its β-D-2'-deoxy-2'-substituted Erythro-pentofuranosyl Nucleoside; 2'-substituted Ribosylation)

The thymine or cytosine type analogs are trimethylsilylated under standard conditions such as hexamethyldisilazane (HMDS) and an acid catalyst (ie. ammonium chloride) and then treated with 3,5-O-ditoluoyl-2-deoxy-2-substituted-α-D-erythro-pentofuranosyl chloride in the presence of Lewis acid catalysts (ie. stannic chloride, iodine, boron tetrafluoroborate, etc.). A specific procedure has recently been described by J. N. Freskos, *Nucleosides & Nucleotides* 8:1075–1076 (1989) in which copper (I) iodide is the catalyst employed.

EXAMPLE 10

Chemical Conversion of an Adenine or Guanine (Purine Type Base) to its β-D-2'-deoxy-2'-substituted Erythro-pentofuranosyl Nucleoside; 2'-substituted Ribosylcation)

The protected purine type analogs are converted to their sodium salts via sodium hydride in acetonitrile and are then treated with 3,5-O-ditoluoyl-2-deoxy-2-substituted-α-D-erythro-pentofuranosyl chloride at ambient temperature. A specific procedure has recently been described by R. K. Robins et al., *Journal of American Chemical Society* 106:6379 (1984).

EXAMPLE 11

Conversion of 2'-deoxy-2-substituted Thymidines to the Corresponding 2'-deoxy-2'-substituted Cytidines (Chemical Conversion of an Tyrimidine type 4-keto Group to an 4-amino group)

The 3',5'-sugar hydroxyls of the 2'modified nucleoside types are protected by acyl groups such as toluoyl, benzoyl, p-nitrobenzoyl, acetyl, isobutryl, trifluoroacetyl, etc. using standards conditions of the acid chlorides or anhydrides and pyridine/dimethylaminopyridine solvent and catalyst. The protected nucleoside is now chlorinated with thionyl chloride or phosphoryl chloride in pyridine or other appropriate basic solvents. The pyrimidine type 4-chloro groups or now displaced with ammonium in methanol. Deprotection of the sugar hydroxyls also takes place. The amino group is benzoylated by the standard two-step process of complete benzylation (sugar hydroxyls and amino group) and the acyls are selectively removed by aqueous sodium hydroxide solution. Alternatively, the in situ process of first treating the nucleoside with chlorotrimethylsilane and base to protect the sugar hydroxyls from subsequent acylation may be employed. K. K. Ogilvie, *Can J. Chem.* 67:831–839 (1989). Another conversion approach is to replace the pyrimidine type 4-chloro group with an 1,2,4-triazolo group which remains intact throughout the oligonucleotide synthesis on the DNA synthesizer and is displaced by ammonium during the ammonium hydroxide step which removes the oligonucleotide from the CPG support and deprotection of the heterocycles. Furthermore, in many cases the pyrimidine type 4-chloro group can utilized as just described and replaced at the end of the oligonucleotide synthesis.

EXAMPLE 12

Procedure for the Attachment of 2'-deoxy-2'-substituted 5'-dimethoxytriphenylmethyl Ribonucleosides to the 5'-hydroxyl of Nucleosides Bound to CPG Support The 2'-deoxy-2'-substituted nucleosides that will reside in the terminal 3'-position of certain antisense oligonucleotides is protected as their 5'-DMT (the cytosine and adenine exocyclic amino groups are benzoylated and the guanine amino is isobutyrylated) and treated with trifluoro-acetic acid/bromoacetic acid mixed anhydride in pyridine and dimethylaminopyridine at 50° C. for five hours. The solution is evaporated under reduced pressure to a thin syrup which is dissolved in ethyl acetate and passed through a column of silica gel. The homogenous fractions were collected and evaporated to dryness. A solution of 10 ml of acetonitrile, 10 micromoles of the 3'-O-bromo-methylester modified pyrimidine nucleoside, and one ml of pyridine/dimethylaminopyridine (1:1) is syringed slowly (60 to 90 sec) through a one micromole column of CPG thymidine (Applied Biosystems, INC.) that had previously been treated with acid according to standard conditions to afford the free 5'-hydroxyl group. Other nucleoside bound CPG columns could be employed. The eluent is collected and syringed again through the column. This process is repeated three times. The CPG column is washed slowly with 10 ml of acetonitrile and then attached to an ABI 380B nucleic acid synthesizer. Oligonucleotide synthesis is now initiated. The standard conditions of concentrated ammonium hydroxide deprotection that cleaves the thymidine ester linkage from the CPG support also cleaves the 3',5' ester linkage connecting the pyrimidine modified nucleoside to the thymidine that was initially bound to the CPG nucleoside. In this manner, any 2'-substituted nucleoside or generally any nucleoside with modifications in the heterocycle and/or sugar can be attached at the very 3'-end of an oligonucleotide sequence.

EXAMPLE 13

Procedure for the Conversion of 2'-deoxy-2'-substituted Ribonucleoside-5'-DMT-3'-phosphoramidites into Oligonucleotides The polyribonucleotide solid phase synthesis procedure of B. S. Sproat, et al., Nucleic Acids Research 17: 3373–3386 (1989) is utilized to prepare the 2'-modified oligonucleotides.

Oligonucleotides of the sequence CGA CTA TGC AAG TAC (SEQ ID NO:1) having 2'-deoxy-2'-fluoro substituent nucleotides were incorporated at various positions within this sequence. In a first oligonucleotide each of the adenosine nucleotides at positions 3, 6, 10, 11 and 14 (counted in a 5' to 3' directed) were modified to include a 2'-deoxy-2'-fluoro moiety. In a further oligonucleotide, the adenosine and the uridine nucleotides at positions 3, 5, 6, 7, 10, 11, 13 and 14 were so modified. In even a further oligonucleotide, the adenosine, uridine and cytidine nucleotides at positions 1, 3, 4, 5, 6, 7, 9, 10, 11, 13 and 14 were so modified and in even a further oligonucleotide, the nucleotides (adenosine, uridine, cytidine and guanosine) at every position was so modified. Additionally an oligonucleotide having the sequence CTC GTA CCT TCC GGT CC (SEQ ID NO:2) was prepared having adenosine, uridine and cytidine nucleotides at positions 1, 2, 3, 5, 6, 7, 8, 9, 10, 11, 12, 15 and 16 also modified to contain 2'-deoxy-2'-fluoro substituent moieties.

Various oligonucleotides were prepared that incorporated nucleotides having 2'-deoxy-2'-methylthio substituents. For ascertaining the coupling efficiencies of 2'-deoxy-2'-methylthio bearing nucleotides into oligonucleotides, the trimer TCC and the tetramer TUU U were synthesized. In the trimer, TCC, the central cytidine nucleotide (the second nucleotide) included a 2'-deoxy-2'-methylthio substituent. In the tetramer, each of the uridine nucleotides included a 2'-deoxy-2'-methylthio substituent. In further oligonucleotides, 2'-deoxy-2'-methylthio substituent bearing nucleotides were incorporated within the oligonucleotide sequence in selected sequence positions. Each of the nucleotides at the remaining sequence positions incorporated a 2'-O-methyl substituent on its nucleotide. Thus all of the nucleotides within the oligonucleotide included a substituent group thereon, either a 2'-deoxy-2'-methylthio substituent or a 2'-O-methyl substituent. These oligonucleotides are: GAG CUC CCA GGC (SEQ ID NO:3) having 2'-deoxy-2'-methylthio substituents at positions 4, 5, 6, 7 and 8; CGA CUA UGC AAG UAC (SEQ ID NO:4) having 2'-deoxy-2'-methylthio substituents at positions 1, 4, 5, 7, 9 and 13; UCC AGG UGU CCG AUC (SEQ ID NO:5) having 2'-deoxy-2'-methylthio substituents are positions 1, 2, 3, 7, 9, 10, 11 and 14; TCC AGG CCG UUU C (SEQ ID NO:6) having 2'-deoxy-2'-methylthio substituents at positions 10, 11 and 12; and TCC AGG TGT CCC C (SEQ ID NO:7) having 2'-deoxy-2'-methylthio substituents at positions 10, 11 and 12.

EXAMPLE 14

Preparation of 2'-Deoxy-2'-fluoro Modified Phosphorothioates Oligonucleotides

2'-Deoxy-2'-substituted 5'-DMT nucleoside 3'-phosphoramidites prepared as described in Examples 1–7 were inserted into sequence-specific oligonucleotide phosphorothioates as described by S. Beaucage et al., Journal of American Chemical Society 112:1253–1255 (1990) and B. S. Sproat, et al., Nucleic Acids Research 17:3373–3386 (1989).

Oligonucleotides of the sequence CGA CTA TGC AAG TAC (SEQ ID NO:7) having phosphorothioate backbone linkages and 2'-deoxy-2'-fluoro substituent nucleotides were incorporated at various positions within this sequence. In a first oligonucleotide each of the backbone linkages was a phosphorothioate linkage and each of the adenosine, uridine and cytidine nucleotides at positions 1, 3, 4, 5, 6, 7, 9, 10, 11, 13 and 14 (counted in a 5' to 3' directed) were modified to include a 2'-deoxy-2'-fluoro moiety. In a further oligonucleotide each of the backbone linkages was a phosphorothioate linkages and the nucleotides (adenosine, uridine, cytidine and guanosine) at every position were modified to include a 2'-deoxy-2'-fluoro moiety.

EXAMPLE 15

Preparation of 2'-Deoxy-2'-fluoro Modified Phosphate Methylated Oligonucleotides The protection, tosyl chloride mediated methanolysis, and mild deprotection described by L. H. Koole et al., in the Journal of Organic Chemistry 54:1657–1664 (1989), is applied to 2'-substituted oligonucleotides to afford phosphate-methylated 2'-substituted oligonucleotides.

EXAMPLE 16

Hybridization Analysis
A. Evaluation of the thermodynamics of hybridization of 2'-modified oligonucleotides.

The ability of the 2'- modified oligonucleotides to hybridize to their complementary RNA or DNA sequences was determined by thermal melting analysis. The RNA complement was synthesized from T7 RNA polymerase and a template-promoter of DNA synthesized with an Applied Biosystems, Inc. 380B RNA species was purified by ion exchange using FPLC (LKB Pharmacia, Inc.). Natural antisense oligonucleotides or those containing 2'-modifications at specific locations were added to either the RNA or DNA complement at stoichiometric concentrations and the absorbance (260 nm) hyperchromicity upon duplex to random coil transition was monitored using a Gilford Response II spectrophotometer. These measurements were performed in a buffer of 10 mM Na-phosphate, pH 7.4, 0.1 mM EDTA, and NaCl to yield an ionic strength of 10 either 0.1 M or 1.0 M. Data was analyzed by a graphic representation of $1/T_m$ vs ln[Ct], where [Ct] was the total oligonucleotide concentration. From this analysis the thermodynamic para-meters were determined. Based upon the information gained concerning the stability of the duplex of heteroduplex formed, the placement of nucleotides containing 2'-deoxy-2'-substituents into oligonucleotides were assessed for their effects on helix stability. Modifications that drastically alter the stability of the hybrid exhibit reductions in the free energy (delta G) and decisions concerning their usefulness as antisense oligonucleotides were made.

As is shown in the following Table 1, the incorporation of 2'-deoxy-2'-fluoro nucleotides into oligonucleotides resulted in significant increases in the duplex stability of the modified oligonucleotide strand (the antisense strand) and its complementary RNA strand (the sense strand). In both phosphodiester backbone and phosphorothioate backbone oligonucleotides, the stability of the duplex increased as the number of 2'-deoxy-2'-fluoro containing nucleotides in the antisense strand increased. As is evident from Table 1, without exception, the addition of a 2'-deoxy-2'-fluoro bearing nucleotide, irrespective of the individual substituent bearing nucleotide or irrespective of the position of that nucleotide in the oligonucleotide sequence, resulted in a increase in the duplex stability.

In Table 1, the underline nucleotides represent nucleotides that include a 2'-deoxy-2'-fluoro substituent. The non-underlined nucleotides are normal nucleotides. The oligonucleotides prefaced with the designation "ps" have a phosphorothioate backbone. Unlabeled oligonucleotides are normal phosphodiester backboned oligonucleotides.

Delta Tm's of greater than 20° C. were measured. By modifying the backbone to a phosphorothioate backbone even greater delta Tm's were observed. In this instance delta Tm's greater than 31° C. were measured. These fluoro substituted oligonucleotides exhibited a consistent and additive increase in the thermodynamic stability of the duplexes formed with RNA. While we do not wish to be bound by theory, it is presently believed that the presence of the 2'-fluoro substituent results in the sugar moiety of 2'-fluoro substituted nucleotide assuming substantially a 3'-endo conformation and this results in the oligonucleotide-RNA duplex assuming an A-type helical conformation.

B. Fidelity of hybridization of 2'-modified oligonucleotides

The ability of the 2'-modified antisense oligonucleotides to hybridize with absolute specificity to the targeted mRNA was shown by Northern blot analysis of purified target mRNA in the presence of total cellular RNA. Target mRNA was synthesized from a vector containing the cDNA for the target mRNA located downstream from a T7 RNA polymerase promoter. Synthesized mRNA was electrophoresed in an agarose gel and transferred to a suitable support membrane (ie. nitrocellulose). The support membrane was blocked and probed using [$^{32}$P]-labeled antisense oligonucleotides. The stringency was determined by replicate blots and washing in either elevated temperatures or decreased ionic strength of the wash buffer. Autoradiography was performed to assess the presence of heteroduplex formation and the autoradiogram quantitated by laser densitometry (LKB Pharmacia, Inc.). The specificity of hybrid formation was determined by isolation of total cellular RNA by standard techniques and its analysis by agarose electrophoresis, membrane transfer and probing with the labeled 2'-modified oligonucleotides. Stringency was predetermined for the unmodified antisense oligonucleotides and the conditions used such that only the specifically targeted mRNA was capable of forming a heteroduplex with the 2'-modified oligonucleotide.

C. Base-Pair Specificity of oligonucleotides and RNA

Base-pair specificity of 2-deoxy-2'-fluoro modified oligonucleotides with the RNA complement (a "Y strand") was determined by effecting single base-pair mismatches and a bulge. The results of these determinations are shown in Table 2. An 18 mer "X strand" oligonucleotide containing 14 adenosine, uridine and cytidine nucleotides having a

TABLE 1

EFFECTS OF 2'-DEOXY-2'-FLUORO MODIFICATIONS ON DNA(ANTISENSE) RNA(SENSE) DUPLEX STABILITY

| Antisense Sequence | | G°37 (kcal/mol) | G°37 (kcal/mol) | Tm(°C.) | Tm(°C.) | Tm(°(C.) /subst |
|---|---|---|---|---|---|---|
| CGA CTA TGC AAG TAC | (SEQ ID N0:1) | −10.31 ± 0.04 | | 45.1 | | |
| CGA CTA TGC AAG TAC | (SEQ ID N0:1) | −13.61 ± 0.08 | −3.50 ± 0.09 | 53.0 | +7.9 | +1.6 |
| CGA CUA UGC AAG UAC | (SEQ ID N0:8) | −16.18 ± 0.08 | −6.07 ± 0.09 | 58.9 | +13.8 | +1.7 |
| CGA CUA UGC AAG UAC | (SEQ ID N0:8) | −19.85 ± 0.05 | −9.74 ± 0.06 | 65.2 | +20.1 | +1.8 |
| ps(CGA CTA TGC AAG TAC) | (SEQ ID N0:7) | −7.58 ± 0.06 | | 33.9 | −11.2 | |
| ps(CGA CUA UGC AAG UAC) | (SEQ ID N0:8) | −15.90 ± 0.34 | −8.32 ± 0.34 | 60.9 | 27.0 | +2.5 |
| CTC GTA CCT TCC GGT CC | (SEQ ID N0:2) | −14.57 ± 0.13 | | 61.6 | | |
| CUC GUA CCU UCC GGU CC | (SEQ ID N0:9) | −27.81 ± 0.05 | −13.24 ± 0.14 | 81.6 | +20.0 | +1.4 |

As is evident from Table 1, the duplexes formed between RNA and an oligonucleotides containing 2'-deoxy-2'-fluoro substituted nucleotides exhibited increased binding stability as measured by the hybridization thermodynamic stability.

2'-deoxy-2'-fluoro substituent was hybridized with the RNA complement "Y strand" in which the 10 position was varied. In Table 2, the underline nucleotides represent nucleotides that include a 2'-deoxy-2'-fluoro substituent.

TABLE 2

EFFECTS OF SINGLE BASE MISMATCHES ON 2'-DEOXY-2'-FLUORO MODIFIED DNA · RNA DUPLEX STABILITY

| Y | base-pair type | G°37 (kcal/mol) | G°37 (kcal/mol) | Tm (°C.) | Tm (°C.) |
|---|---|---|---|---|---|
| | X strand: deoxy(CTC GTA CCT TTC CGG TCC) | | | | |
| | Y strand: ribo(³'GAG CAU GGY AAG GCC AGG⁵') | | | | |
| A | Watson-Crick | −14.57 ± 0.13 | | 61.6 | |
| C | T—C mismatch | −12.78 ± 0.11 | 1.79 ± 0.17 | 54.4 | −7.2 |
| G | T—G inismatch | −16.39 ± 0.25 | −1.82 ± 0.28 | 61.7 | 0.1 |
| U | T—U mismatch | −13.48 ± 0.17 | 1.09 ± 0.22 | 55.9 | −5.7 |
| none | bulged T | −14.86 ± 0.35 | −0.284 ± 0.37 | 59.4 | −2.2 |
| | X strand: deoxy(CUC GUA CCU UUC CGG UCC) | | | | |
| | Y strand: ribo(³'GAG CAU GGY AAG GCC AGG⁵') | | | | |
| A | Watson-Crick | −27.80 ± 0.05 | | 81.6 | |
| C | U—C mismatch | −21.98 ± 0.28 | 5.82 ± 0.28 | 73.8 | −7.8 |
| G | U—G mismatch | −21.69 ± 0.16 | 6.12 ± 0.17 | 77.8 | −3.8 |
| U | U—U mismatch | −18.68 ± 0.15 | 9.13 ± 0.16 | 73.6 | −8.0 |
| none | bulged U | −22.87 ± 0.27 | 4.94 ± 0.27 | 75.5 | −6.2 |

As is evident from Table 2, the 2'-deoxy-2'-fluoro modified oligonucleotide formed a duplex with the RNA complement with greater specificity than a like sequenced unmodified oligonucleotide.

EXAMPLE 17

Nuclease Resistance

A. Evaluation of the resistance of 2'-modified oligonucleotides to serum and cytoplasmic nucleases.

Natural phosphorothioate, and 2-modified oligonucleotides were assessed for their resistance to serum nucleases by incubation of the oligonucleotides in media containing various concentrations of fetal calf serum or adult human serum. Labeled oligonucleotides were incubated for various times, treated with protease K and then analyzed by gel electrophoresis on 20% polyacrylamine-urea denaturing gels and subsequent autoradiography. Autoradiograms were quantitated by laser densitometry. Based upon the location of the modifications and the known length of the oligonucleotide it was possible to determine the effect on nuclease degradation by the particular 2'-modification. For the cytoplasmic nucleases, a HL60 cell line was used. A post-mitochondrial supernatant was prepared by differential centrifugation and the labeled oligonucleotides were incubated in this supernatant for various times. Following the incubation, oligo-nucleotides were assessed for degradation as outlined above for serum nucleolytic degradation. Autoradiography results were quantitated for comparison of the unmodified, the phosphorothioates, and the 2'-modified oligonucleotides. Utilizing these test systems, the stability of a 15-mer oligonucleotide having 2-deoxy-2'-fluoro substituted nucleotides at positions 12 and 14 and a phosphorothioate backbone was investigated. As a control, an unsubstituted phosphodiester oligonucleotide was 50% degraded within 1 hr and 100% degraded within 20 hours. In comparison for the 2'-deoxy-2'-fluoro substituted oligonucleotide having the phosphorothioate backbone, degradation was limited to less than 10% after 20 hours.

B. Evaluation of the resistance of 2'-modified oligonucleotides to specific endo- and exo-nucleases.

Evaluation of the resistance of natural and 2'-modified oligonucleotides to specific nucleases (ie, endonucleases, 3',5'-exo-, and 5',3'-exonucleases) was done to determine the exact effect of the modifications on degradation. Modified oligonucleotides were incubated in defined reaction buffers specific for various selected nucleases. Following treatment of the products with proteinase K, urea was added and analysis on 20% poly-acrylamide gels containing urea was done. Gel products were visualized by staining using Stains All (Sigma Chemical Co.). Laser densitometry was used to quantitate the extend of degradation. The effects of the 2'-modifications were determined for specific nucleases and compared with the results obtained from the serum and cytoplasmic systems.

What is claimed is:

1. A mixed sequence oligonucleotide having at least one modified 2'-deoxyfuranosyl moiety modified by substitution with bromo, chloro, iodo, azido, amino, substituted amino, bromomethyl, chloromethyl, iodomethyl, cyanato, bromoalkoxyl, chloroalkoxyl, iodoalkoxyl, alkyl sulfide, alkyl sulfonate, nitrate or nitrite.

2. A mixed sequence oligonucleotide having at least one 2'-deoxyfuranosyl moiety modified by substitution with alkyl.

3. The oligonucleotide or oligonucleotide analog of claim 1 having from about 5 to about 50 nucleotide bases.

4. The oligonucleotide or oligonucleotide analog of claim 1 wherein said modification is at the 3' end of said oligonucleotide.

5. The oligonucleotide or oligonucleotide analog of claim 1 wherein at least one of the sugar linking groups is replaced with carbon or ether linkages.

6. The oligonucleotide or oligonucleotide analog of claim 5 wherein a 5'-methylene group and carbocyclic sugar are removed.

7. The oligonucleotide or oligonucleotide analog of claim 1 further modified such that at least some of the sugar linking groups comprise a phosphorothioate, methyl phosphonate, or phosphate alkylate.

8. The oligonucleotide or oligonucleotide analog of claim 1 in a pharmaceutically acceptable carrier.

* * * * *

UNITED STATES PATENT AND TRADEMARK OFFICE
CERTIFICATE OF CORRECTION

PATENT NO. : 6,307,040 B1  
DATED : October 23, 2001  
INVENTOR(S) : Phillip Dan Cook and Andrew M. Kawasaki Page 1 of 1

It is certified that error appears in the above-identified patent and that said Letters Patent is hereby corrected as shown below:

Column 35,  
Line 52, please delete the words "azido, amino, substituted amino".

Column 36,  
Lines 61-66, add the following claims:

9. The mixed sequence oligonucleotide of claim 3 wherein said alkyl is $C_1$ to $C_{12}$ straight or branched chain alkyl.

10. The mixed sequence oligonucleotide of claim 3 wherein said alkyl includes unsaturation.

Signed and Sealed this

Thirtieth Day of April, 2002

Attest:

JAMES E. ROGAN  
*Attesting Officer*

*Director of the United States Patent and Trademark Office*

SEQUENCE LISTING

<160> NUMBER OF SEQ ID NOS: 12

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: nucleoside
      having a modified sugar moiety

<400> SEQUENCE: 1
cgactatgca agtac                                                      15

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: nucleoside
      having a modified sugar moiety

<400> SEQUENCE: 2
ctcgtacctt ccggtcc                                                    17

<210> SEQ ID NO 3
<211> LENGTH: 12
<212> TYPE: RNA
<213> ORGANISM: Artificial Sequence
<220> FEATURE:
<223> OTHER INFORMATION: Description of Artificial Sequence: nucleoside
      having a modified sugar moiety

<400> SEQUENCE: 3
gagcucccag gc                                                              12

<210> SEQ ID NO 4
<211> LENGTH: 15
<212> TYPE: RNA
<213> ORGANISM: Artificial Sequence
<220> FEATURE:
<223> OTHER INFORMATION: Description of Artificial Sequence: nucleoside
      having a modified sugar moiety

<400> SEQUENCE: 4
cgacuaugca aguac                                                           15

<210> SEQ ID NO 5
<211> LENGTH: 15
<212> TYPE: RNA
<213> ORGANISM: Artificial Sequence
<220> FEATURE:
<223> OTHER INFORMATION: Description of Artificial Sequence: nucleoside
      having a modified sugar moiety

<400> SEQUENCE: 5
uccagguguc cgauc                                                           15

<210> SEQ ID NO 6
<211> LENGTH: 13
<212> TYPE: DNA
<213> ORGANISM: Artificial Sequence
<220> FEATURE:
<223> OTHER INFORMATION: Description of Combined DNA/RNA Molecule:
      Artificial Sequence
<220> FEATURE:
<223> OTHER INFORMATION: Description of Artificial Sequence: nucleoside
      having a modified sugar moiety

<400> SEQUENCE: 6
tccaggccgu uuc                                                             13

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: nucleoside
      having a modified sugar moiety

<400> SEQUENCE: 7
tccaggtgtc ccc                                                             13

<210> SEQ ID NO 8
<211> LENGTH: 15
<212> TYPE: RNA
<213> ORGANISM: Artificial Sequence
<220> FEATURE:
<223> OTHER INFORMATION: Description of Artificial Sequence: nucleoside
      having a modified sugar moiety

<400> SEQUENCE: 8

```
cgacuaugca aguac                                                    15

<210> SEQ ID NO 9
<211> LENGTH: 17
<212> TYPE: RNA
<213> ORGANISM: Artificial Sequence
<220> FEATURE:
<223> OTHER INFORMATION: Description of Artificial Sequence: nucleoside
      having a modified sugar moiety

<400> SEQUENCE: 9
cucguaccuu ccgucc                                                   17

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: nucleoside
      having a modified sugar moiety

<400> SEQUENCE: 10
ctcgtacctt tccggtcc                                                 18

<210> SEQ ID NO 11
<211> LENGTH: 18
<212> TYPE: RNA
<213> ORGANISM: Artificial Sequence
<220> FEATURE:
<223> OTHER INFORMATION: Description of Artificial Sequence: nucleoside
      having a modified sugar moiety

<400> SEQUENCE: 11
gagcauggya aggccagg                                                 18

<210> SEQ ID NO 12
<211> LENGTH: 18
<212> TYPE: RNA
<213> ORGANISM: Artificial Sequence
<220> FEATURE:
<223> OTHER INFORMATION: Description of Artificial Sequence: nucleoside
      having a modified sugar moiety

<400> SEQUENCE: 12
cucguaccuu uccgucc                                                  18
```